United States Patent
Noda et al.

(10) Patent No.: US 8,734,381 B2
(45) Date of Patent: May 27, 2014

(54) METHOD AND SYSTEM FOR SUPPLYING PREDETERMINED GAS INTO BODY CAVITIES OF A SPECIMEN

(75) Inventors: Kenji Noda, Tokyo (JP); Takefumi Uesugi, Tokyo (JP); Daisuke Sano, Tokyo (JP); Atsuhiko Kasahi, Yokohama (JP)

(73) Assignee: Olympus Corporation (JP)

( * ) Notice: Subject to any disclaimer, the term of this patent is extended or adjusted under 35 U.S.C. 154(b) by 2601 days.

(21) Appl. No.: 11/095,390

(22) Filed: Mar. 31, 2005

(65) Prior Publication Data

US 2005/0222491 A1 Oct. 6, 2005

(30) Foreign Application Priority Data

Mar. 31, 2004 (JP) ................. 2004-108363

(51) Int. Cl.
*A61M 37/00* (2006.01)
(52) U.S. Cl.
USPC .............. 604/26; 604/23; 604/24; 604/28
(58) Field of Classification Search
USPC .......................... 604/23, 24, 25, 26
See application file for complete search history.

(56) References Cited

U.S. PATENT DOCUMENTS 5,246,419 A * 9/1993 Absten .................... 604/26
6,299,592 B1 * 10/2001 Zander .................... 604/26

FOREIGN PATENT DOCUMENTS

JP 2000-139827 5/2000

* cited by examiner

*Primary Examiner* — Laura Bouchelle
(74) *Attorney, Agent, or Firm* — Ostrolenk Faber LLP

(57) ABSTRACT

In a gas supply system, a controller is electrically connected to a pressure regulator and an operation switch. The controller is operative to control the pressure regulator so that a predetermined gas is supplied to a first delivery member directing to a first body cavity with its pressure regulated to a first pressure suitable for the first body cavity. The controller is operative to control the pressure regulator depending on an instruction sent from the operation switch upon operation of the operator so that the predetermined gas is supplied to a second delivery member directing to a second body cavity with its pressure regulated to a second pressure suitable for the second body cavity.

20 Claims, 9 Drawing Sheets

METHOD AND SYSTEM FOR SUPPLYING PREDETERMINED GAS INTO BODY CAVITIES OF A SPECIMEN

CROSS REFERENCE TO RELATED APPLICATION

This application is based upon the prior Japanese Patent Application 2004-108363 filed on Mar. 31, 2004 and claims the benefit of priority therefrom so that the descriptions of which are all incorporated herein by reference.

BACKGROUND OF THE INVENTION

1. Field of the Invention

The present invention relates to a method and a system for supplying predetermined gas into body cavities of a specimen.

2. Description of the Related Art

In recent years, laparoscopic surgeries have been practiced extensively. The laparoscopic surgery is executed for treating a patient with minimally invasive capability.

Specifically, in the laparoscopic surgeries, for example, a rigid endoscope, referred to as "rigidscope", for observation is inserted into a body cavity, such as, an abdominal cavity of a patient. A treatment tool is inserted into the abdominal cavity to be guided to a site to be treated therein while an image of the inside of the abdominal cavity, which is obtained by the rigidscope, is observed.

In such a laparoscopic surgery, a first trocar through which an endoscope for observation is guided into a body cavity of a patient, and a second trocar through which a treatment tool is guided to a site to be treated are inserted to an abdominal part of the patient.

In order to ensure the endoscope field and a space to manipulate the treatment tool, insufflation gas is injected into the abdominal cavity through at least one of the first and second trocar, or another trocar.

While the abdominal cavity is distended by the insufflation gas, an image inside the abdominal is picked up by the endoscope inserted thereinto via the first trocar, which allows an operator to treat the site to be treated in the patient while observing the site and the treatment tool based on the image.

As insufflation gas, for example, carbon dioxide gas (hereinafter also referred to as $CO_2$) has been used, which can be easily absorbed into a living body. Insufflators each supplying carbon dioxide gas have been developed.

During operation of such an insufflator, a state wherein carbon dioxide gas flows through a gas delivery member and another stare wherein a flow of the carbon dioxide gas passing through the gas delivery member is blocked have repeatedly appeared.

Specifically, a controller of the insufflator is configured to detect a pressure inside the abdominal cavity of the patient with a pressure sensor. In addition, the controller is configured to monitor a difference between a predetermined pressure value for the patient and a current pressure inside of the abdominal cavity of the patient, which is detected by the pressure sensor, thereby adjusting a flow-rate of the carbon dioxide gas based on the difference.

For example, Japanese Unexamined Patent Publication No. 2000-139827 discloses a gas supply apparatus for endoscopes. The gas supply apparatus is used for supplying air into a body cavity, such as a stomach or the like, to check a state of an affected site in the body cavity.

With the disclosed gas supply apparatus, one end of a connecting tube coupled to and extending from a connecting port of the apparatus is coupled to a forceps inlet communicating with a treatment tool channel. Furthermore, a foot switch is electrically connected to the gas supply apparatus. The foot switch allows an operator to manipulate the gas supply apparatus remotely.

Accordingly, the operator operates at least one of the foot switch and a gas supply switch mounted on the apparatus to allow air to be delivered from the connecting port of the apparatus and supplied through the connecting tube, the forceps inlet and the treatment tool channel into a body cavity.

Recently, new attempts have been undertaken to utilize, while a first endoscope is inserted to the abdominal cavity in a patient through a trocar, therapeutic procedure in which an insert portion of a second endoscope is inserted to a lumen, such as the stomach, the large intestine, or the like, of the patient. The therapeutic procedure allows an operator to specify a site to be treated by visually referring to images picked up by the first endoscope and the second endoscope, respectively.

Even in such a case, insufflation gas for lumens, such as air, is fed into the lumen through the second endoscope inserted thereinto to distend the lumen. When the air is supplied into the lumen, however, it is difficult for the air to be absorbed into the living body. This may cause the lumen to remain inflated.

For this reason, in cases of insufflating gas into a lumen, such as the large intestine of a living body, using an endoscope $CO_2$ regulator (hereinafter referred to as ECR) has been considered. The ECR is designed to output carbon dioxide gas ($CO_2$), which is absorbed easily into the living body.

SUMMARY OF THE INVENTION

The present invention has been made on the background.

According to one aspect of the present invention, there is provided a gas supply system for supplying predetermined gas to a first body cavity of a specimen through a first delivery member and to a second body cavity of the specimen through a second delivery member. The gas supply system has a pressure regulator coupled to the first and second delivery members and configured to regulate a pressure of the predetermined gas to a first pressure and a second pressure. The first pressure is suitable for the first body cavity. The second pressure is suitable for the second body cavity. The pressure regulator allows the predetermined gas with its pressure regulated to be supplied to both the first and second delivery members. The gas supply system has an operation switch operable by an operator; and a controller electrically connected to the pressure regulator and the operation switch and operative to control the pressure regulator so that the predetermined gas is supplied to the first delivery member with its pressure regulated to the first pressure. The controller is operative to control the pressure regulator depending on an instruction sent from the operation switch upon operation of the operator so that the predetermined gas is supplied to the second delivery member with its pressure regulated to the second pressure.

According to another aspect of the present invention, there is provided a gas supply system for supplying predetermined gas to a first body cavity of a specimen through a first delivery member and to a second body cavity of the specimen through a second delivery member. The gas supply system has means for regulating a pressure of the predetermined gas to a first pressure suitable for the first body cavity to supply to the first body cavity the predetermined gas with its pressure regulated to the first pressure. The gas supply system has means for sending an instruction based upon operation of an operator, and means for determining whether the instruction sent from the sending means is accepted based on a pressure inside the first body cavity. The gas supply system has means for regulating the pressure of the predetermined gas to a second pressure suitable for the second body cavity to supply to the second body cavity the predetermined gas with its pressure regulated to the second pressure when it is determined that the instruction sent from the sending means is accepted.

According to a further aspect of the present invention, there is provided an observation system. The observation system has a gas supply system for supplying predetermined gas to a first body cavity of a specimen through a first delivery member and to a second body cavity of the specimen through a second delivery member. The gas supply system includes a pressure regulator coupled to the first and second delivery members and configured to regulate a pressure of the predetermined gas to a first pressure and a second pressure. The first pressure is suitable for the first body cavity. The second pressure is suitable for the second body cavity. The pressure regulator allows the predetermined gas with its pressure regulated to be supplied to both the first and second delivery members. The gas supply system has an operation switch operable by an operator, and the controller. The controller is electrically connected to the pressure regulator and the operation switch. The controller is operative to control the pressure regulator so that the predetermined gas is supplied to the first delivery member with its pressure regulated to the first pressure. The controller is operative to control the pressure regulator depending on an instruction sent from the operation switch upon operation of the operator so that the predetermined gas is supplied to the second delivery member with its pressure regulated to the second pressure. In addition, the observation system has an observation device integrated with a gas delivery channel and configured to be inserted into the second body cavity of the specimen to observe an inside of the second body cavity. The gas delivery channel serves as part of the second delivery member.

According to a still further aspect of the present invention, there is provided a method of insufflating predetermined gas to a first body cavity of a specimen through a first delivery member and to a second body cavity of the specimen through a second delivery member using an operation switch operable by an operator. The method includes supplying the predetermined gas to the first gas delivery member with the pressure of the predetermined gas regulated to a first pressure suitable for the first body cavity. The method includes sending an instruction based upon operation of the operation switch by the operator. The method includes determining whether a pressure inside the first body cavity rises up to a predetermined pressure setting or thereabout. The method includes ignoring the instruction to continuously supply the predetermined gas to the first gas delivery member when it is determined that the pressure inside the first body cavity does not rise up to the predetermined pressure setting or thereabout.

BRIEF DESCRIPTION OF THE DRAWINGS

Various aspects of the present invention will be more particularly described with reference to the accompanying drawings in which.

DETAILED DESCRIPTION OF EMBODIMENTS OF THE INVENTION

An embodiment of the present invention will be described hereinafter with reference to the accompanying drawings.

Figure 1:
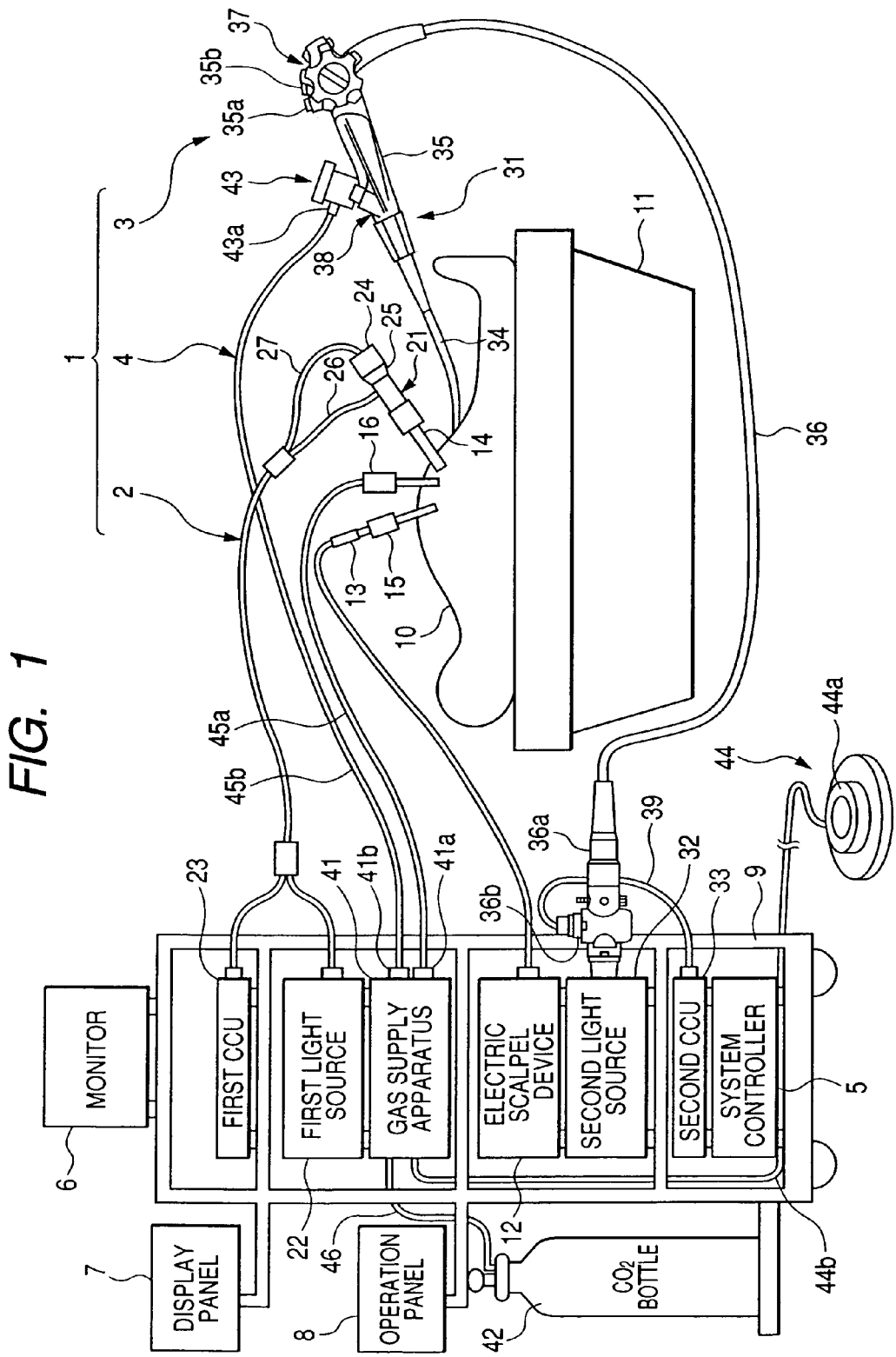
FIG. 1 is an overall structural view schematically illustrating the structure of an endoscopic surgical system equipped with a gas supply apparatus according to an embodiment of the present invention.

As shown in FIG. 1, a laparoscopic surgery system, referred to as a surgical system hereinafter, 1 has a first endoscope system 2, a second endoscope system 3, and a gas supply system 4 according to an embodiment of the present invention.

The surgical system 1 has a system controller 5, a monitor 6 as a display device, a center display panel 7, a center operation panel 8, and a movable cart (trolley) 9.

Reference numeral 10 designates a patient as a specimen, and reference numeral 11 designates an operation table that allows the patient 11 to lie thereon. Reference numeral 12 designates an electric scalpel device as an example of operation devices, which is mounted on the cart 9. The surgical system 1 has an electric scalpel 13 serving as an operation tool. The electric scalpel 13 is electrically connected to the electric scalpel device 12.

Reference numerals 14, 15, and 16 designate first, second, and third trocars, which are inserted into, for example, an abdominal portion of the patient 10, respectively. The first trocar 14 allows an endoscope, described herein after, of the first endoscope system 2 to be guided into a first body cavity, such as an abdominal cavity AC (see FIG. 2) of the patient 10. The abdominal cavity AC, which means a cavity separated by the diaphragm from the thoracic cavity above and by the plane of the pelvic inlet from the pelvic cavity below, serves as a first body cavity of the patient 10 according to the embodiment.

The second trocar 15 permits guide of a treatment tool into the abdominal cavity AC. The treatment tool, such as the electric scalpel 13, is operative to remove and/or treat a tissue corresponding to at least one site to be treated in the abdominal cavity AC.

The third trocar 16 allows gas for the abdominal cavity, such as carbon dioxide gas, to be introduced into the abdominal cavity AC. The carbon dioxide gas, referred to as "$CO_2$" can be easily absorbed into a living body, such as the patient 10, which is supplied from the gas supply system 4. The carbon dioxide gas can be introduced into the inside of the abdominal cavity AC through at least one of the trocars 14 and 15.

The first endoscope system 2 includes a rigid endoscope 21 as a first endoscope with, for example, a rigid insert portion at one end thereof. The rigid endoscope 21 is referred to as "rigidscope" hereinafter. The first endoscope system 2 includes a first light source 22, a first camera control unit, referred to as "first CCU" hereinafter, and a camera for endoscopes.

One end portion of the insertion portion (not shown) of the rigidscope 21, for example, is configured to be inserted in part into the first trocar 14. The rigidscope 21 is provided with an illumination optics (not shown) and an observation optics (not shown), which are installed in the one end portion of the insertion portion. The illumination optics is composed of, for example, a light guide and the like, and configured to illuminate light onto a target, such as the site to be treated, of the inside of the patient 10. For example, the observation optics is composed of relay lenses and the like. The observation optics is configured to optically deliver an optical image of the target illuminated by the light.

The rigidscope 21 is provided at the other end side of the insertion portion with an eyepiece 25 that allows an operator to observe the optical image delivered by the observation optics. The camera 24 is detachably installed in the eyepiece 25. The camera 24 is integrated with an image pickup device, such as a CCD (Charge Coupled Device) or the like, having a light sensitive pixel area, wherein the optical image delivered by the observation optics is focused on the light sensitive pixel area thereof. The optical image of the target focused on the light sensitive pixel area of the image pickup device is photoelectrically converted into an electric signal as a first image signal, by the image pickup device.

The first endoscope system 2 is provided with a light guide cable 26 extending from one side of the other end of the rigidscope 21. The light guide cable 26 is optically coupled to the first light source 22, allowing optical coupling between the rigidscope 21 and the first light source 22. The first endoscope system 2 is provided with an image pickup cable 27 electrically connecting between the first CCU 23 and the camera 24.

The first light source 22 has a function of supplying illumination light to the illumination optics of the rigidscope 21 via the light guide cable 26. The first CCU 23 is operative to execute electrical drive control of the image pickup device. When the first image signal corresponding to the optical image of the target, which is picked up by the image pickup device, is sent to the first CCU 23, the first CCU 23 is operative to receive the first image signal to subject the received first image signal to image processing of necessity. The first CCU 23 is operative to output the image-processed first image signal to at least one of the monitor 6 and the center display panel 7.

These operations allow at least one of the monitor 6 and the center display panel 7 to display a first image of the target thereon based on the first image signal. That is, the first image is an endoscopic image corresponding to the first image signal picked up by the rigidscope 21.

The second endoscope system 3 includes a flexible endoscope 31 as a second endoscope with, for example, a flexible insert portion 34 at one end thereof. The flexible insert portion is so flexible that it can be inserted into a lumen BC as a second body cavity, such as the large intestine of the patient. In the specification, the lumen is defined as the cavity of an organ in a specimen, such as the cavity of the stomach, the cavity of the large intestine, the cavity of a blood vessel, or the like in the specimen. The flexible endoscope 31 is referred to as "flexible scope" hereinafter. The second endoscope system 3 includes a second light source 32, and a second CCU 33.

The flexiblescope 31 has a substantially hollow-rod (tubular) shape, which is narrow in diameter and flexible. The flexiblescope 31 is internally formed with a gas delivery channel SC (see FIG. 2).

Specifically, the flexiblescope 31 is provided at its one end with the insert portion 34 to be inserted at its one end into the interior of the lumen BC, and a manipulator 35 whose one end is joined to the other end of the insert portion 34. The manipulator 35 allows, for example, an operator to manipulate the flexiblescope 31. The flexiblescope 31 is provided with a universal cord 36 whose one end is joined to the other end of the manipulator 35.

The manipulator 35 is provided with a gas and water supply switch 35a mounted thereon. The gas and water supply switch 35a is formed with a through hole, also referred to as "gas and water supply channel), communicated with the gas delivery channel SC inside of the manipulator 35. The gas and water supply switch 35a, the gas delivery channel SC, and the insert portion 34 allow the operator to supply gas and water therethrough.

It should be noted that the term "operator" through the specification is not necessarily limited to a person who actually treats; the term "operator" refers to a concept that involves any of nurses or other operators who assist such a treatment action.

The manipulator 35 is provided with a suction switch 35b disposed thereto and a flexion knob 35c that allows the operator to flex a flexible portion (not shown) of the flexiblescope 31. The manipulator 35 is formed with a treatment tool channel 34a communicated with the gas delivery channel SC, and the flexiblescope 31 is provided with a treatment tool insertion opening 38 formed to be communicated with the treatment tool channel 34a in the manipulator 35. The treatment tool insertion opening 38 allows treatment tools to be inserted therethrough. The other end of the universal cord 36 is coupled to a light source connector 36a optically detachably so that the universal cord 36 is optically coupled to the second light source 32 through the light source connector 36a.

In the embodiment, for example, the treatment tool channel 34a is larger than the gas and water supply channel in inner diameter, and is shorter than the gas and water supply channel in axial length.

The second light source 32 has a light source and an optical system (that are not shown) so that illumination light supplied from the second light source 32 is transferred to the flexiblescope 31 through the light source connector 36a and the universal cord 36.

The flexiblescope 31 is provided at its one end of the insertion portion 34 with an illumination optics. The illumination optics is composed of a light guide that can illuminate light on a target inside the patient 10, such as the lumen BC, through an illumination window disposed to one side of the one end of the insertion portion 34.

The flexiblescope 31 is provided with an image pickup device, such as a CCD (Charge Coupled Device) or the like, installed in the one end of the insertion portion 34. The image pickup device has a light sensitive pixel area. The image pickup device is so arranged that an optical image of the target illuminated by the light outputted from the illumination optics is focused on the light sensitive pixel area of the image pickup device.

The image pickup device of the flexiblescope 31 is electrically connected to the second CCU 33 through the universal cord 36 and the like. Reference numeral 39 is an electric cable electrically connecting between an electric connector 36b attached to the light source connector 36a and the second CCU 33.

The image pickup device is operative to photoelectrically convert the optical image of the target focused on the light sensitive pixel area into an electric signal as a second image signal.

The second CCU 33 is operative to execute electrical drive control of the image pickup device. When the second image signal corresponding to the optical image of the target, which is picked up by the image pickup device, is sent to the second CCU 33 through the electric cable 39, the second CCU 33 is operative to receive the second image signal to subject the received first image signal to image processing of necessity. The second CCU 33 is operative to output the image-processed second image signal to at least one of the monitor 6 and the center display panel 7.

These operations allow at least one of the monitor 6 and the center display panel 7 to display a second image of the target thereon based on the second image signal. That is, the second image is an endoscopic image corresponding to the second image signal picked up by the flexiblescope 31.

Turning now to the gas supply system 4, it includes a gas supply apparatus 41, a carbon dioxide gas cylinder ($CO_2$ bottle) 42 as a supplier, and an insertion adapter, referred to simply as adapter, 43. The gas supply system 4 has a foot switch 44 serving as an operation switch for controlling supply of the carbon dioxide gas into the lumen BC, an abdominal cavity tube 45a, and a lumen tube 45b. The $CO_2$ bottle 42 stores carbon dioxide in liquid.

The gas supply apparatus 41 is provided with a first adapter (connector) 41a for insufflation into the abdominal cavity AC and a second adapter 41b for insufflation into the lumen BC. The first adapter 41a is airtightly coupled to one end of the abdominal cavity tube 45a. The other end of the abdominal cavity tube 45a is airtightly coupled to the third trocar 16. The second adapter 41b is airtightly coupled to one end of the lumen tube 45b. The other end of the lumen tube 45b is airtightly coupled to a tube coupler 43a formed on one side of the adapter 43, which allows the lumen tube 45b to be communicated with the gas delivery channel SC inside the flexiblescope 31 through the adapter 43.

The foot switch 44 is. provided with a switch portion 44a and is configured to provide instructions to instruct supply of the carbon dioxide gas into the lumen BC to the gas supply apparatus 41 while the operator or the like depresses the switch portion 44a with operator's foot or the like.

The gas supply apparatus 41 and the $CO_2$ bottle 42 is coupled to each other through a high-pressure gas tube 46. The gas supply apparatus 41 and the foot switch 44 are electrically connected to each other through a foot switch cable 44b. The electrical connection between the foot switch 44 and the gas supply apparatus 41 can be established by wireless. Each of the tubes 45a and 45b is made of a material such as, for instance, silicone, Teflon®, or other similar materials.

The system controller 5 is operative to perform control of the whole system 1. With the system controller 5, the center display panel 7, the center operation panel 8, and peripheral devices including the electric scalpel device 12, the first light source 22, the second light source 32, the first CCU 23, the second CCU 33, and the gas supply apparatus 41 are communicably connected through communication buses (not shown), respectively.

The monitor 6 has a function of receiving the first and second image signals outputted from the first and second CCUs 23 and 33 to display at least one of the first and second images thereon based on the received first and second image signals.

The center display panel 7 is composed of a display screen, such as a liquid crystal screen or the like. The center display panel 7 allows concentrative display of operating states of the peripheral devices together with the first and second images on the display screen.

The center operation panel 8 is designed to a touch panel and composed of a display section, such as a liquid crystal screen or the like, and a touch-sensitive device integrally formed on the display screen. The display section of the center operation panel 8 has a display function of providing a setting screen on which operable switches (buttons) for the peripheral devices are graphically displayed. The display section has an operating function of operating the operable switches by touching them. The center operation panel 8 is electrically connected to the system controller 5.

Specifically, the operator touches at least one of the operable switches with, for example, a finger so that the touch-sensitive device sets operating conditions corresponding to at least one of the touched operable switches to remotely send to the system controller 5 instructions for operating a corresponding one of the peripheral devices based on the set operating conditions. These remote operations of the graphical operable switches on the center operation panel 8 with respect to the peripheral devices are substantially identical with direct operations of operable switches directly attached to the peripheral devices.

The peripheral devices including the electric scalpel device 12, the first and second light sources 22 and 32, the first and second CCUs 23 and 33, and the gas supply apparatus 41 are mounted on the cart 9. In addition, the system controller 5, the center display panel 7, the center operation panel 8 are mounted on the cart 9.

Next, a structure of the gas supply apparatus 41 will be described hereinafter with reference to FIG. 2.

Figure 2:
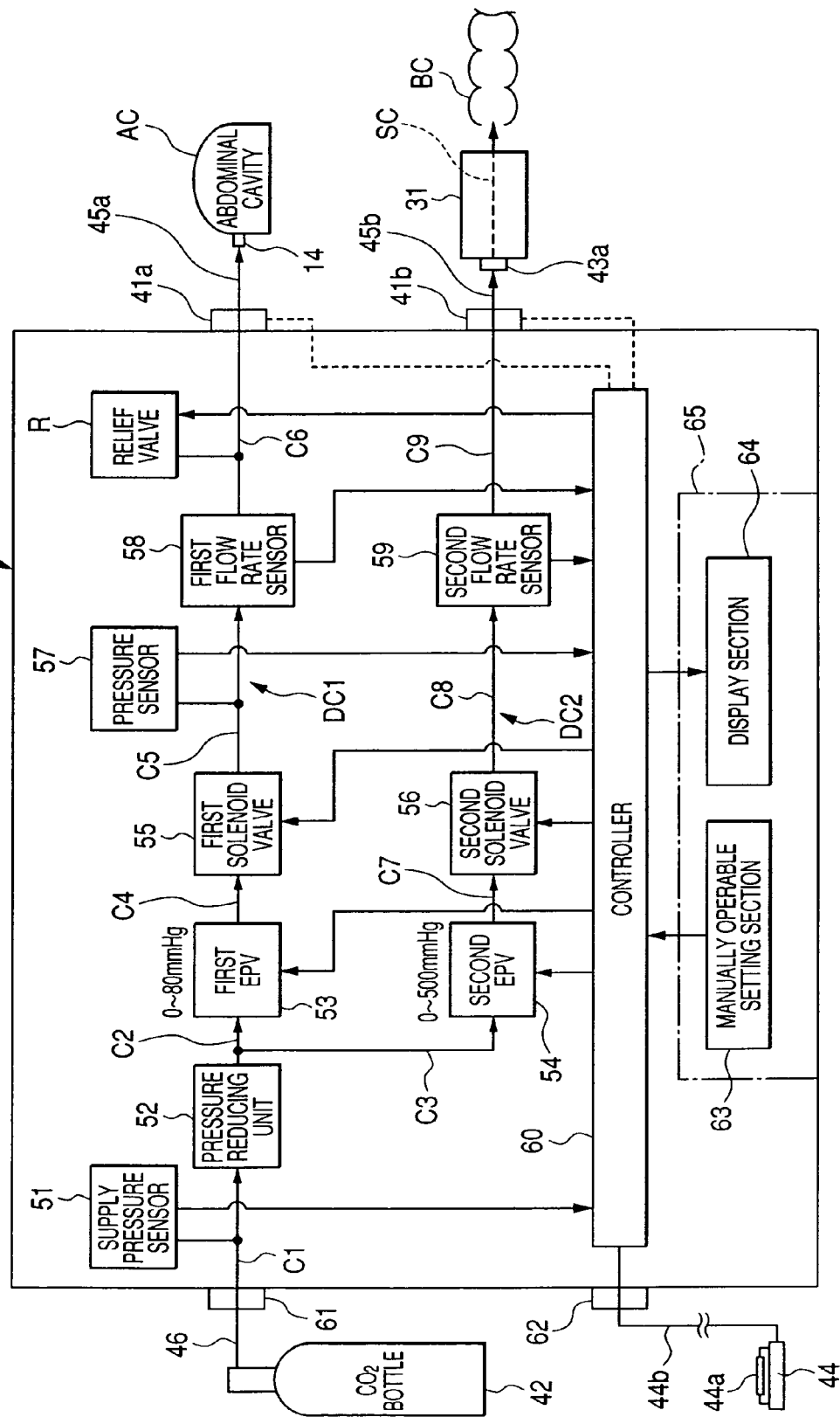
FIG. 2 is a block diagram illustrating a schematic structure of the gas supply apparatus illustrated in FIG. 1.

As shown in FIG. 2, the gas supply apparatus 41 includes first to ninth delivery channels C1 to C9, a supply pressure sensor 51, a pressure reducing unit 52 serving as, for example, a pressure regulator. The gas supply apparatus 41 includes first and second electropneumatic proportional valves (EPVs) 53 and 54 as examples of pressure regulating valves, serving as the pressure regulator, and first and second electromagnetic valves (solenoid valves) 55 and 56 as examples of open/close valves. The first and second electromagnetic valves 55 and 56 serves as the pressure regulator.

The gas supply apparatus 41 includes a pressure sensor 57, first and second flow-rate sensors 58 and 59, and a controller 60.

Moreover, the gas supply apparatus 41 is provided with a high-pressure adapter 61, a switch connector 62, and a manually operable setting section 63 and a display section 64 in addition to the first and second adapters 41a and 41b.

Specifically, the $CO_2$ bottle 42 has a discharge port (cock) to which one end of the high-pressure gas tube 46 is joined. The other end of the high-pressure gas tube 46 is joined to the high-pressure adapter 61. The high-pressure adapter 61 is joined to an inlet of the pressure reducing unit 52 via the first delivery channel C1. The supply pressure sensor 51 is attached to the first delivery channel C1. An outlet of the pressure reducing unit 52 is branched into the second delivery channel C2 for the abdominal cavity AC and the third delivery channel C3 for the lumen BC.

One branched channel C2 is coupled to an inlet of the first electropneumatic proportional valve 53. An outlet of the first electropneumatic proportional valve 53 is coupled to an inlet of the first solenoid valve 55 via the fourth delivery channel C4. An outlet of the first solenoid valve 55 is coupled to the fifth delivery channel C5 to which the pressure sensor 57 is attached. The fifth delivery channel C5 is coupled to an inlet of the first flow rate sensor 58 whose outlet is coupled through the sixth delivery channel C6 and the first adapter 41a to the one end of the abdominal cavity tube 45a. The other end of the tube 45a is coupled to the third trocar 16, and the third trocar 16 is inserted into the abdominal cavity AC of the patient 10.

The other branched channel C3 is coupled to an inlet of the second electropneumatic proportional valve 54. An outlet of the second electropneumatic proportional valve 54 is coupled to an inlet of the second solenoid valve 56 via the seventh delivery channel C7. An outlet of the second solenoid valve 56 is coupled to the eighth delivery channel C8. The eighth delivery channel C8 is coupled to an inlet of the second flow rate sensor 59 whose outlet is coupled through the ninth delivery channel C9 and the second adapter 41b to the one end of the lumen tube 45b. The other end of the tube 45b is communicably coupled to the gas delivery channel SC formed inside the flexiblescope 31 through the tube coupler 43a, and the insertion portion 34 of the flexiblescope 31 is inserted into the lumen BC of the patient 10.

In the embodiment, the first electropneumatic proportional valve 53, the fourth delivery channel C4, the first solenoid valve 55, the fifth delivery channel C5, the first flow-rate sensor 58, the first adapter 41a, and the abdominal cavity tube 45a constitute a first $CO_2$ supply path DC1 directing the carbon dioxide gas into the abdominal cavity AC. Specifically, the first electropneumatic proportional valve 53 and the first solenoid valve 55 are provided in the first $CO_2$ supply path DC1 so that the first solenoid valve 55 is located at downstream of the first electropneumatic proportional valve 53.

Similarly, the second electropneumatic proportional valve 54, the seventh delivery channel C7, the second solenoid valve 56, the eighth delivery channel C8, the second flow-rate sensor 59, the second adapter 41b, the lumen tube 45b, the tube coupler 43a, and the gas delivery channel SC constitute a second $CO_2$ supply path DC2. The second $CO_2$ supply path DC2 is configured to direct the carbon dioxide gas into the lumen BC. Specifically, the second electropneumatic proportional valve 54 and the second solenoid valve 56 are provided in the second $CO_2$ supply path DC2 so that the second solenoid valve 56 is located at downstream of the second electropneumatic proportional valve 54.

The gas supply apparatus 41 has the foot switch cable 44b electrically connected to the switch connector 62; the foot switch cable 44b is electrically connected to the foot switch 44. The switch connector 62 is electrically connected to the controller 60. With the electrical connection between the foot switch 44 and the controller 60, the depressing operation of the switch portion 44a by the operator allows the instruction to be provided through the foot switch cable 44b to the controller 60. Incidentally, communications between the foot switch 44 and the controller 60 can be wirelessly established.

The manually operable setting section 63 and the display section 64 are provided on a front panel (panel section) 65 electrically connected to the controller 60.

The supply pressure sensor 51 is electrically connected to the controller 60. The supply pressure sensor 51 has a function of detecting the pressure of the carbon dioxide gas evaporated from the $CO_2$ bottle 42 and flowing through the first delivery channel C1 to send the detected result (detected pressure value) to the controller 60.

The pressure reducing unit 52 is operative to reduce the pressure of the carbon dioxide gas supplied through the first delivery channel C1 to a predetermined pressure.

The first electropneumatic proportional valve 53 is provided with a solenoid composed of, for example, a magnet coil (solenoid coil) and a compass needle, which are not shown. The first electropneumatic proportional valve 53 is provided with a thin film for pressure control, and a pressure reducing spring. The solenoid is electrically connected to the controller 60. The first electropneumatic proportional valve 53 is configured such that the solenoid controls force applied on the thin film by the pressure reducing spring depending on a control signal applied from the controller 60, thereby regulating the pressure of the carbon dioxide gas.

Specifically, the first electropneumatic proportional valve 53 is designed to change its opening in proportional to a voltage or a current as the control signal applied from the controller 60 so as to regulate the pressure of the carbon dioxide gas flowing therethrough within a corresponding appropriate range.

For example, the first electropneumatic proportional valve 53 allows the pressure of the carbon dioxide gas to be regulated within a range from 0 to 80 mmHg or thereabout based on the control signal applied from the controller 60.

The second electropneumatic proportional valve 54 has, for example, substantially the same structure as the first electropneumatic proportional valve 53. Specifically, the second electropneumatic proportional valve 54 is operative to regulate the pressure of the carbon dioxide gas flowing therethrough within a corresponding appropriate range. For example, the second electropneumatic proportional valve 54 allows the pressure of the carbon dioxide gas to be regulated within a range from 0 to 500 mmHg or thereabout based on the control signal applied from the controller 60.

The gas supply pressure range of approximately 0 to 80 mmHg for insufflation of the carbon dioxide gas into the abdominal cavity AC is established as one example a pressure range suitable for insufflation inside the abdominal cavity AC. Similarly, the gas supply pressure range of approximately 0 to 500 mmHg for insufflation of the carbon dioxide gas into the lumen BC is established as one example a pressure range suitable for insufflation inside the lumen BC.

Each of the first and second solenoid valves 55 and 56 is electrically connected to the controller 60 and configured to open and close based on control signals sent from the controller 60. The opening and closing of the first solenoid valve 55 allow the fifth delivery channel C5 (the first $CO_2$ supply path DC1) to open and close, respectively. Similarly, the opening and closing of the second solenoid valve 56 permit the eighth delivery channel C8 (the second $CO_2$ supply path DC2) to open and close, respectively.

The first and second flow rate sensors 58 and 59 are electrically connected to the controller 60. The first flow rate sensor 58 has a function of detecting the flow rate of the carbon dioxide gas flowing through the first solenoid valve 55 and the fifth delivery channel C5. Similarly, the second flow rate sensor 59 is operative to detect the flow rate of the carbon dioxide gas flowing through the second solenoid valve 56 and the eighth delivery channel C8. Each of the first and second flow rate sensors 58 and 59 is configured to send the detected result to the controller 60.

The controller 60 is operative to receive the measured values outputted from the supply pressure sensor 51, the pressure sensor 57, the first and second flow rate sensors 58 and 59. The controller 60 is programmed to execute opening control (pressure control) of each of the first and second electropneumatic proportional valves 53 and 54, opening and closing controls of each of the first and second solenoid valves 55 and 56, and display control of the display section 64 based on the received measured values.

In addition, the manually operable setting section 63 is electrically connected to the controller 60. The controller 60 is also programmed to execute opening control (pressure control) of the first and second electropneumatic proportional valve 53 and 54, opening and closing controls of each of the first and second solenoid valves 55 and 56, and display control of the display section 64 based on the instructions sent from the manually operable setting section 63.

Specifically, when the cock of the $CO_2$ bottle 42 is opened, carbon dioxide stored therein in a liquid form is vaporized to form the carbon dioxide gas. The carbon dioxide gas is delivered to the pressure reducing unit 52 through the high-pressure gas tube 46, the high pressure adapter 61, and the first delivery channel C1 of the gas supply apparatus 41. The carbon dioxide gas is reduced in pressure by the pressure reducing unit 52 to have a predetermined pressure. Thereafter, the carbon dioxide gas is selectively switched to either second delivery channel C2 and the first $CO_2$ supply path DC1, which direct to the abdominal cavity AC, or the third delivery channel C3 and the second $CO_2$ supply path DC2, which directs to the lumen BC, depending on the control signals sent from the controller 60.

Furthermore, the gas supply apparatus 41 is provided with a relief valve (opening and closing valve) R disposed at the midstream of the sixth delivery channel C6 between the first flow rate sensor 38 and the first adapter 41a. The relief valve R is electrically connected to the controller 60. The relief valve R is operative to remain in a closed state, and to open based on a control signal sent from the controller 60 when the measured value of the pressure sensor 57 exceeds a predetermined threshold value by a predetermined value or more. The opening of the relief valve R causes carbon dioxide gas in the abdominal cavity AC to be released, thereby reducing a pressure inside the abdominal cavity AC. Like the abdominal cavity side, a relief valve can be provided at the midstream of the ninth delivery channel C9 between the second flow rate sensor 59 and the second adapter 41b.

Incidentally, in the embodiment, the channels and the like constituting the first $CO_2$ supply path DC1 provide airtight junction therebetween, and the channels and the like constituting the second $CO_2$ supply path DC2 provide airtight junction therebetween.

Figure 3:
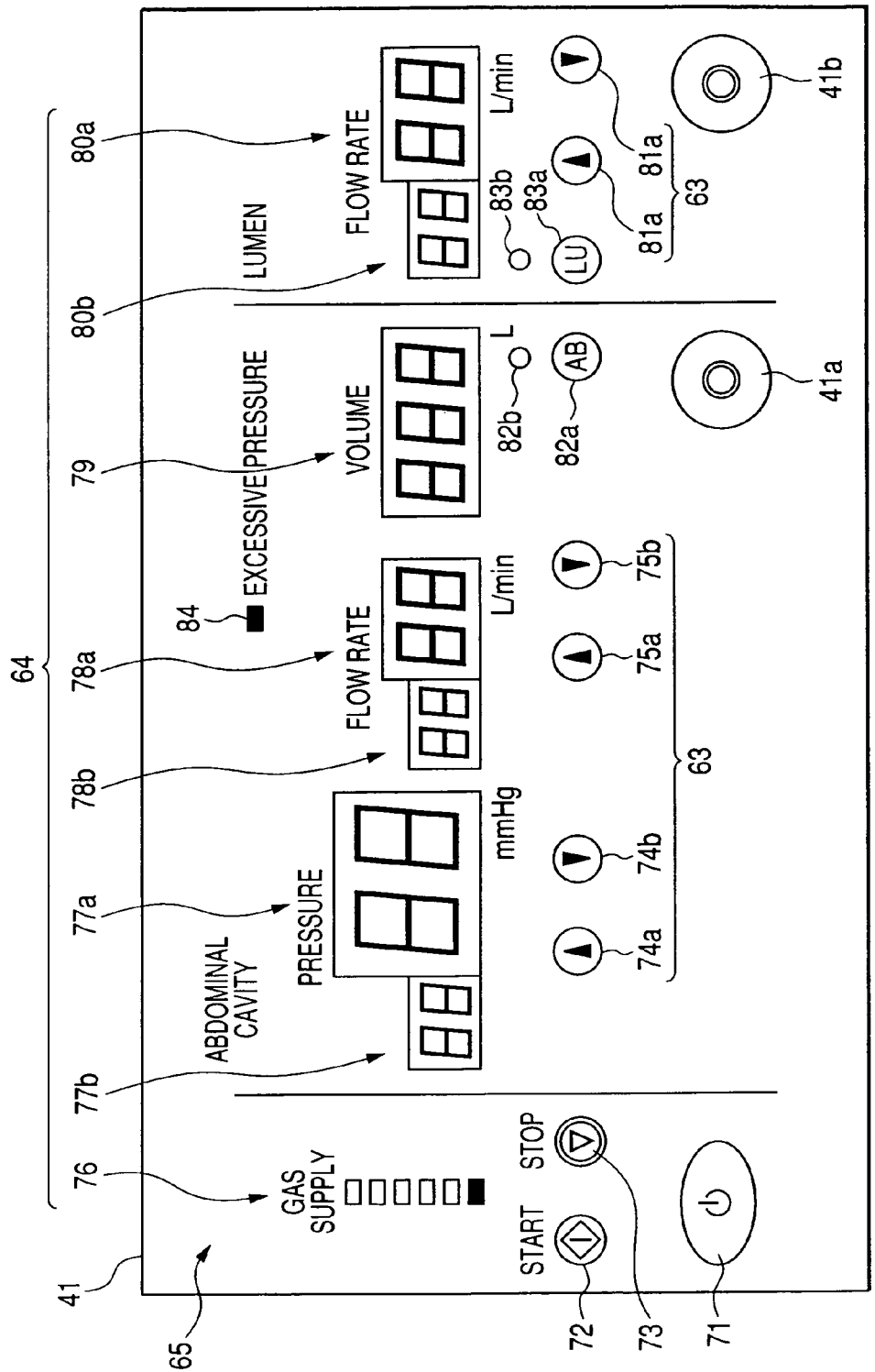
FIG. 3 is a view schematically illustrating a configuration example of a manually operable setting section and a display section provided on a front panel of the gas supply apparatus illustrated in FIG. 1.

In the embodiment, as shown in FIG. 3, the panel section (front panel 65) on which the manually operable setting section 41 and the display section 42 are provided is attached to one side of a housing of the gas supply apparatus 41, to which the first and second adapters 41a and 41b are attached.

The manually operable setting section 63 and the display section 42 are graphically displayed on the front panel 65 of the gas supply apparatus 41.

The manually operable setting section 63 includes a power switch 71, a gas-supply start button 72, a gas-supply stop button 73, pressure setting buttons 74a and 74b for the pressure inside the abdominal cavity AC, and flow-rate setting buttons 75a and 75b for the abdominal cavity AC. The manually operable setting section 63 includes flow-rate setting buttons 81a and 81b for the lumen BC, an abdominal cavity select switch (button) 82a (see "AB" in FIG. 3), and a lumen select switch (button) 83a (see "LU" in FIG. 3).

The display section 64 includes gas remaining volume indicators 76, pressure displays 77a and 77b for the pressure inside the abdominal cavity AC, and flow-rate displays 78a and 78b for the abdominal cavity AC. The display section 64 includes a total volume display 79 for the abdominal cavity AC, flow-rate displays 80a and 80b for the lumen BC, an abdominal-cavity insufflation mode indicator 82b, a lumen insufflation mode indicator 83b, and an excessive pressure indicator 84.

The power switch 71 serves as a switch that permits the operator to turn power on and off to the apparatus 41. The gas-supply start button 72 serves as a button that allows the operator to send an instruction to start insufflation of the carbon dioxide gas into the abdominal cavity AC to the controller 60. The gas-supply stop button 73 serves as a button that permits the operator to send an instruction to stop the insufflation of the carbon dioxide gas to the controller 60.

The pressure setting button 74a and the flaw-rate setting buttons 75a and 81a serve as buttons that allow the operator to send instructions to increase the corresponding parameters, respectively.

Specifically, every time the operator clicks the pressure setting button 74a, a pressure setting inside the abdominal cavity AC turns up. Similarly, every time the operator clicks the flow-rate setting button 75a, a flow-rate setting of the carbon dioxide gas to be insufflated into the abdominal cavity AC turns up. Every time the operator clicks the flow-rate setting button 81a, a flow-rate setting of the carbon dioxide gas to be insufflated into the lumen BC turns up.

The settings of the corresponding parameters (the pressure setting inside the abdominal cavity AC, the flow-rate setting of the carbon dioxide gas directing to the abdominal cavity AC, and the flow-rate setting of the carbon dioxide gas directing to the lumen BC) are sent to the controller 60.

Similarly, the pressure setting button 74b and the flow-rate setting buttons 75b and 81b serve as buttons that allow the operator to send instructions to decrease the corresponding parameters, respectively.

Specifically, every time the operator clicks the pressure setting button 74b, the pressure setting inside the abdominal cavity AC turns down. Similarly, every time the operator clicks the flow-rate setting button 75b, the flow-rate setting of the carbon dioxide gas being insufflated into the abdominal cavity AC turns down. Every time the operator clicks the flow-rate setting button 81b, the flow-rate setting of the carbon dioxide gas being insufflated into the lumen BC turns down.

The settings of the corresponding parameters (the pressure setting inside the abdominal cavity AC, the flow-rate setting of the carbon dioxide gas directing to the abdominal cavity AC, and the flow-rate setting of the carbon dioxide gas directing to the lumen BC) are sent to the controller 60.

The gas remaining volume indicators 76 are vertically arranged so that a top indicator that is lighting indicates the amount of carbon dioxide gas available.

The pressure display 77a is configured to display a pressure value (in mmHg) based on a measured value of the pressure sensor 57. The pressure display 77b is configured to display the pressure setting determined based on the operations of, for example, the pressure setting buttons 74a and 74b.

The flow-rate display 78a is configured to display a flow-rate (in L/min) based on a measured value of the first flow-rate sensor 58. The flow-rate display 78b is configured to display the flow-rate setting determined based on the operations of, for example, the flow-rate setting buttons 75a and 75b.

The total volume display 79 is configured to display a total amount of carbon dioxide gas calculated by the controller 60 based on the measured value of the first flow-rate sensor 58.

The flow-rate display 80a is configured to display a flow-rate (in L/min) based on a measured value of the second flow-rate sensor 59. The flow-rate display 80b is configured to display the flow-rate setting determined based on the operations of, for example, the flow-rate setting buttons 81a and 81b.

When the operator turns on the abdominal cavity select button 82a, the button 82a is configured to send to the controller 60 an instruction to make it execute operations for supplying the carbon dioxide gas into the abdominal cavity AC. In other words, when the operator turns on the abdominal cavity select button 82a, the button 82a is configured to send to the controller 60 an instruction to change the operation mode thereof to an abdominal cavity insufflation mode.

Similarly, when the operator turns on the lumen select button 83a, the button 83a is configured to send to the controller 60 an instruction to make it execute operations for supplying the carbon dioxide gas into the lumen BC. In other words, when the operator turns on the lumen select button 83a, the button 83a is configured to send to the controller 60 an instruction to change the operation mode thereof to a lumen insufflation mode.

The excessive pressure indicator 84 consists of, for example, red LED (light emitting device). The excessive pressure indicator 84 is configured to turn on or flash on and off based on a control signal sent from the controller 60 at anytime the pressure measured by the pressure sensor 57 exceeds a threshold value of the pressure inside the abdominal cavity AC by a predetermined pressure or more. The turning-on or the flashing of the excessive pressure indicator 84 allows the operator to visually recognize that the pressure inside the abdominal cavity AC exceeds the threshold value by the predetermined pressure or more.

Incidentally, the center operation panel 8 allows the operator to set the parameters of the gas supply apparatus 41, which include the setting of the pressure inside the abdominal cavity AC, and the settings of the flow-rates for the abdominal cavity AC and the lumen BC. Specifically, the settings determined on the center operation panel 8 for the corresponding parameters are sent to the controller 60 through the system controller 5. The controller 60 carries out abdominal-cavity pressure control, lumen pressure control, abdominal-cavity flow-rate control, and lumen flow-rate control based on the corresponding parameters, respectively.

In addition, the center display panel 7 can be configured to display at least one of the settings, which has been specified by the operator, displayed on the pressure displays 77a and 77b, flow-rate displays 78a, 78b, 80a, and 80b, and the total volume display 79.

Specifically, the controller 60 operates to send at least one of the settings, which has been specified by the operator, displayed on the pressure displays 77a and 77b, flow-rate displays 78a, 78b, 80a, and 80b, and the total volume display 79 to the system controller 5. The system controller 5 receives at least one of the settins sent from the controller 60 to display it on the center display panel 7.

Incidentally, an excessive pressure indicator, which is the same as the excessive pressure sensor 84, for turning on or flashing on and off at anytime the pressure inside the lumen BC exceeds a threshold value by a predetermined pressure can be provided on the front panel 65 of the gas supply apparatus 41.

Figure 4:
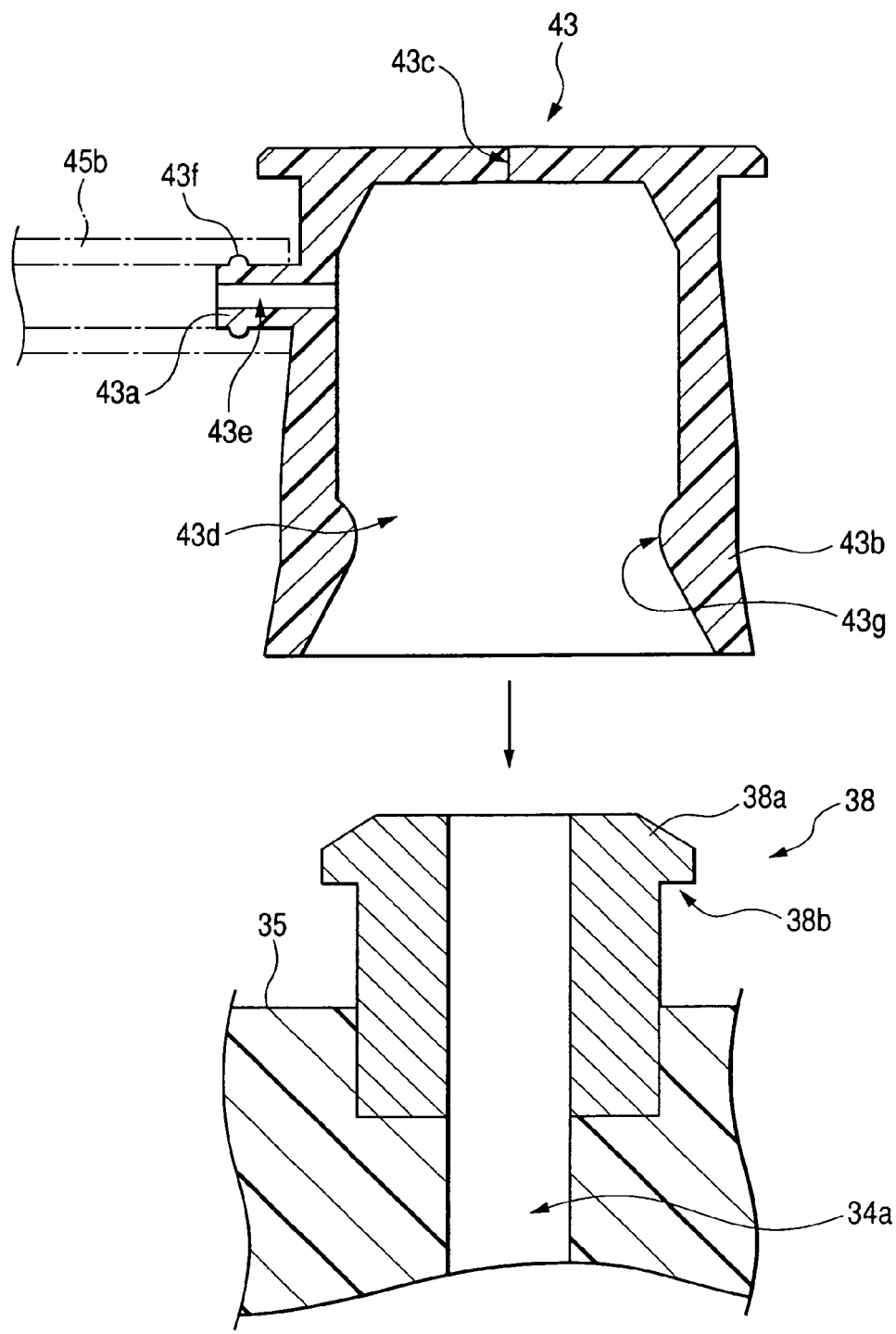
FIG. 4 is a view schematically illustrating a structure of an adapter shown in FIG. 1.

On the other hand, as shown in FIG. 4, the adapter 43 is made of a resin member with elasticity in a substantially cylindrical hollow shape such that its one end is opened and the other end is closed. Specifically, the adapter 43 is composed of a tube coupling portion 43a, a mount portion 43b constituting a side peripheral wall surrounding a hollow space 43d inside the adapter 43, and a slit 43c formed on the other end to be communicated with the hollow space 43d.

The tube coupling portion 43a has a substantially cylindrical shape with an outer peripheral surface configured to closely fit in an inner peripheral surface of the other end of the lumen tube 45b. The tube coupling portion 43a projects from part of the mount portion 43b so that its center axis is orthogonal to the side peripheral wall 43b. The tube coupling portion 43a is formed with a through hole 43e communicated with the hollow space 43d of the adapter 43. In addition, the tube coupling portion 43a is formed with a projecting portion 43f projecting radially around the outer peripheral surface of the tube coupling portion 43a such that the projecting surface becomes a spherically convex surface. The projecting portion 43f allows the lumen tube 45b to be prevented from dropping out of the adapter 43.

Specifically, close fit of the other end of the lumen tube 45b in the tube coupling portion 43a allows the projection portion 43f to press the inner peripheral surface of the other end portion of the tube 45b against its elastic force. Thus, the elastic force of part of the tube 45b on which the projection portion 43f presses causes the tube coupling portion 43a and the lumen tube 45b to be crimped to each other, preventing the lumen tube 45b from dropping out of the tube coupling portion 43a.

The open end of the mount portion 43b of the adapter 43 is configured to be engageble with a cylindrical base 38a attached to one side of the manipulator 35 to project therefrom. The base 38a is formed with the tool insertion opening 38 communicated with the treatment tool channel 34a. The base 38a is provided with a convex portion 38b projecting radially around the outer peripheral surface of the projective end thereof in a step.

Moreover, the mount portion 43b is formed with an inwardly projecting portion 43g projecting inwardly around the inner peripheral surface thereof such that the projecting surface becomes a spherically convex surface. The outer peripheral surface of the convex portion 38b is longer than the inner peripheral surface of the inwardly projecting portion 43g in diameter.

Specifically, the adapter 43 is pressed to be fit from its open end to the base 38a of the manipulator 35 so that the inwardly projecting portion 43 g of the adapter 43 exceeds the convex portion 38b of the base 38a. This configuration allows the outer peripheral surface of the base 38a to press the inwardly projecting portion 43g of the mount portion 43b against the elastic force of the inwardly projecting portion 43g.

Thus, the resilient force of the inwardly projecting portion 43g causes the outer peripheral surface of the base 38a to be fixedly crimped on the inner peripheral surface of the mount portion 43b. Even if the adapter 43 is pulled in a direction the reverse of the press-fit direction, the convex portion 38b of the base 38a can be latched to the inwardly projecting portion 43g of the adapter 43. This makes it possible to prevent the adapter 43 from dropping out of the manipulator 35 (flexiblescope 31).

Coupling the lumen tube 45b to the tube coupling portion 43a with the adapter 43 attached to the base 38a of the manipulator 35 permits the carbon dioxide gas to be supplied into the lumen BC through the tube 45b, the treatment tool channel 34a, and the gas delivery channel SC.

The slit 43c is normally closed due to the resilient force of the closed end of the adapter 43. Press-fitting of an instrument tool into the slit 43c against the resilient force of the closed end of the adapter 43 and insertion thereof into the hollow space 43d allow the instrument tool to be introduced into the lumen BC through the treatment tool channel 34a and the gas delivery channel SC.

In the embodiment, as shown in FIG. 1, the adapter 43 is coupled to the base 38a that corresponds to the communicable connecting location of the lumen tube 45b with respect to the gas delivery channel SC inside the manipulator 35. This configuration allows the adapter 43 to be arranged at a position closer to the insertion section 34 than the gas and water supply switch 35a through which the through hole is formed.

Specifically, in the embodiment, the through hole of the gas and water supply switch 35a of the manipulator 35 of the flexiblescope 31 deviates from the second $CO_2$ supply path DC2 including the lumen tube 45b through which the carbon dioxide gas is supplied. Thus, in the embodiment, the operator is able to perform the operations to supply the carbon dioxide gas into the lumen BC and to interrupt the supply thereof by the operations to depress the switch portion 44a of the foot switch 44 and release it without opening and closing the through hole in the switch 35a.

Next, operations of the surgical system 1 with the gas supply system 4 according to the embodiment will be described hereinafter.

When using the gas supply apparatus 41, an assistant, such as a nurse, prepares the abdominal cavity tube 45a to couple the one end of the tube 45a to the first adapter 41a of the gas supply apparatus 41 and the other end thereof to the third trocar 16, respectively. Next, the assistant presses the adapter 43 to fit to the base 38 of the flexiblescope 31, and prepares the lumen tube 45b to couple the one end of the tube 45b to the second adapter 41b of the gas supply apparatus 41 and the other end thereof to the tube coupling portion 43a of the adapter 43, respectively.

Subsequently, before surgery, the assistant opens the cock of the $CO_2$ bottle 42. The opening of the cock of the $CO_2$ bottle 42 causes the carbon dioxide gas to flow out of the bottle 42 through the high-pressure gas tube 46 so as to flow into the gas supply apparatus 41. The gas flowing into the apparatus 41 is introduced through the first delivery channel C1 to the pressure reducing unit 52.

The carbon dioxide gas is reduced in pressure by the pressure reducing unit 52 to have the predetermined pressure, thereby being guided via the second delivery channel C2 to the inlet of each of the first and second electropneumatic proportional valves 53 and 54.

Under a state before surgery, each of the first and second electropneumatic proportional valves 53 and 54 remains closed, which causes the carbon dioxide gas not to flow any delivery channels downstream of each of the first and second electropneumatic proportional valves 53 and 54.

Next, the power switch 71 is turned on. In response to the turning-on of the switch 71, the pressure display 77a of the panel section 65 is ready to display the measured value by the pressure sensor 57, and the foot switch 44 becomes a state that allows the operator to operate it.

On the pressure display 77b, the pressure setting inside the abdominal cavity AC, which is previously set on, for example, the center operation panel 8, is displayed. Similarly, on the flow-rate display 78b, the flow-rate setting of the carbon dioxide gas to be insufflated into the abdominal cavity AC, which is previously set on, for example, the center operation panel 8, is displayed. Furthermore, on the flow-rate display 80b, the flow-rate setting of the carbon dioxide gas to be insufflated into the lumen BC, which is previously set on, for example, the center operation panel 8, is displayed.

The supply pressure sensor 51 measures the pressure supplied from the $CO_2$ bottle 42 to the pressure reducing unit 52 through the first delivery channel C1 to send the measured value to the controller 60. As a result, the controller 60 calculates the volume of the carbon dioxide gas remaining in the $CO_2$ bottle 42 to display it on the gas remaining volume indicators 76.

In cases where no pressure setting inside the abdominal cavity AC is previously determined on the center operating panel 8, the operator appropriately operates the pressure setting buttons 74a and 74b to determine the pressure setting inside the abdominal cavity AC. The instruction corresponding to the pressure setting inside the abdominal cavity AC is sent from the manually operable setting section 63 to the controller 60. Similarly, in cases where no flow-rate settings for the insufflations into the abdominal cavity AC and the lumen BC are previously determined on the center operating panel 8, the operator appropriately operates the flow-rate setting buttons 75a, 75b, 81a, and 81b.

These operations of buttons 75a, 75b, 81a, and 81b allow determination of the flow-rate settings for insufflations into the abdominal cavity AC and the lumen BC, respectively. The instructions corresponding to the flow-rate settings to be insufflated into the abdominal cavity AC and the lumen BC, respectively, are sent from the manually operable setting section 63 to the controller 60.

Subsequently, the operator inserts the third trocar 16 into a desired position in the abdominal cavity AC by a predetermined length. Incidentally, the position in the abdominal cavity AC where the third trocar 16 reaches and the length of the trocar to be inserted into the abdominal cavity AC vary depending on the state of the patient 10 and the site to be treated.

While the third trocar 16 is inserted in the abdominal cavity AC so that the carbon dioxide gas is delivered through the first $CO_2$ supply path DC1 into the abdominal cavity AC, the pressure sensor 57 measures the pressure inside the abdominal cavity AC through the first $CO_2$ supply path DC1. As a result, the controller 60 causes the pressure display 77a to display the measured pressure.

Next, the operator manipulates the flexiblescope 31 wherein the body cavity tube 45b has already coupled to the manipulator 35 thereof to insert the insertion portion 34 from, for example, the anus of the patient 10 into a desired position in the lumen BC inside the abdominal cavity AC, such as the large intestine thereof. Incidentally, the position in the lumen BC where the insertion portion 34 reaches and the length to be inserted into the lumen BC vary depending on the state of the patient 10 and the site to be treated.

Like the third trocar 16, the operator inserts the first trocar 14 in which the insertion portion of the rigidscope 21 is inserted into a desired position in the abdominal cavity AC by a predetermined length.

While the third trocar 16 and the rigidscope 21 are inserted in the abdominal cavity AC, and the flexible endoscope 31 is inserted in the lumen BC, the operator selectively operates any one of the abdominal cavity select button 82a and the lumen select button 83a to determine the operation mode of the controller 60.

For example, when the operator wants to insufflate the carbon dioxide gas into the abdominal cavity AC, the operator turns on the abdominal cavity select button 82a. The tuning-on of the button 82a causes the controller 60 to enter an abdominal cavity insufflation mode and to keep the lumen select button 83a off.

On the other hand, when the operator wants to insufflate the carbon dioxide gas into the lumen BC, the operator turns on the lumen select button 83a. The turning-on of the button 83a causes the controller 60 to enter a lumen insufflation mode and to keep the abdominal cavity select button 82a off.

Next, an example of control operations of the controller 60 of the gas supply apparatus 41 when insufflating the carbon dioxide gas into each of the abdominal cavity AC and the lumen BC will be described hereinafter with reference to FIGS. 5 and 6.

While the controller 60 is in the abdominal-cavity insufflation mode due to the turning-on operation of the abdominal cavity select button 82a by the operator, when an assistant or the like turns on the gas-supply start button 72, the manually operable setting section 63 provides the instruction corresponding to the turning-on operation of the button 72 to the controller 60.

The controller 60 receives the instruction corresponding to the turning-on operation of the button 72 to determine whether its operation mode is the abdominal-cavity insufflation mode (step S1).

Because the abdominal cavity select button 82a is in on state, the controller 60 determines its operation mode is the abdominal-cavity insufflation mode, in other words, the determination in step S1 is YES.

Subsequently, the controller 60 sends the control signals to the first electropneumatic proportional valve 53, and the first and second solenoid valves 55 and 56, respectively. These control signals allow the carbon dioxide gas supplied up to the inlet of the first electropneumatic proportional valve 53 to flow through the first electropneumatic proportional valve 53 so that the pressure and the flow-rate of the carbon dioxide gas are regulated within the corresponding predetermined ranges suitable for the insufflation of the abdominal cavity AC, respectively. The carbon dioxide gas with its pressure and flow-rate being regulated, respectively, passes through the first solenoid valve 55 to be supplied into the abdominal cavity AC through the first adapter 41a, the abdominal cavity tube 45a, and the third trocar 16.

Repeatedly generating a gas flow state and a gas flow interrupting state allows flow-rate control of the carbon dioxide gas supplied through the first adapter 41a to be realized.

Specifically, the controller 60 obtains the pressure value inside the abdominal cavity AC based on the pressure measured by the pressure sensor 57 with the first solenoid valve 55 closed, thereby displaying the obtained pressure value on the pressure display 77a in step S2.

The controller 60 determines whether the obtained pressure value reaches the pressure setting displayed on the pressure display 77b (step S3).

When determining that the obtained pressure does not reach the pressure setting, that is, the determination in step S3 is NO, the controller 60 calculates the difference between the obtained pressure and the pressure setting to determine a pressure reduction value of the first electropneumatic proportional valve 53 based on the calculated difference (step S4).

Subsequently, the controller 60 delivers the control signal to the second solenoid valve 56 to close it (step S5), and sends the control signal to the first solenoid valve 55 to open it (step S6). Next, the controller 60 sends the control signal to the first electropneumatic proportional valve 53 to open it by a predetermined opening corresponding to the determined pressure reduction value (step S7).

As a result, the carbon dioxide gas, which is reduced in pressure to the predetermined pressure by the pressure reduction unit 52, is supplied into the abdominal cavity AC through the first $CO_2$ supply path DC1. Specifically, the carbon dioxide gas with the predetermined pressure is supplied through the first electropneumatic proportional valve 53, the fourth flow channel C4, the first solenoid valve 55, the fifth flow channel C5, the first flow rate sensor 58, the sixth flow channel C6, and the first adapter 41a. Thereafter, the carbon dioxide gas with the predetermined pressure is delivered through the abdominal cavity tube 45a and the third trocar 16 to be supplied into the abdominal cavity AC.

Under such a gas supply state, the pressure of the carbon dioxide gas measured by the supply pressure sensor 51, that of the carbon dioxide gas measured by the pressure sensor 57, and the flow-rate of the carbon dioxide gas measured by the first flow-rate sensor 58 are sent to the controller 60. The controller 60 calculates the gas remaining volume, the flow-rate of the carbon dioxide gas insufflating into the abdominal cavity AC, and the total amount of the carbon dioxide gas stored therein based on the measured values.

The controller 60 executes display control of the panel section 65 to display the calculated gas remaining volume, the flow-rate of the carbon dioxide gas, and the total amount thereof on the gas remaining volume indicators 76, the flow-rate display 78a, and the total volume display 79, respectively.

After a predetermined period of time has elapsed, the controller 60 sends the control signal to the first solenoid valve 55 to close it, thereby interrupting the insufflation of the carbon dioxide gas into the abdominal cavity AC (step S8). The controller 60 determines whether the gas-supply stop button 73 is turned on (step S9).

When the obtained pressure inside the abdominal cavity AC does not reach the pressure setting, because the operator does not turn on the gas-supply stop button 73, the determination in step S9 is NO. Thus, the controller 60 shifts to step S1 and repeatedly executes the carbon dioxide gas supply and interruption control operations for the abdominal cavity AC shown in steps S1 to S9 as long as the controller 60 is in the abdominal-cavity insufflation mode. The whole of the carbon dioxide gas supply and interruption control operations for the abdominal cavity AC is referred to as "abdominal-cavity pressure control operations".

Incidentally, while repeatedly executing the abdominal-cavity pressure control operations shown in steps S1 to S9, because the second solenoid valve 56 has already closed, the controller 60 executes no operation in step S5.

While the controller 60 repeatedly executes the abdominal-cavity pressure control operations shown in steps S1 to S9 in the abdominal-cavity insufflation mode, when the instruction depending on the turning-on operation of the switch portion 44a of the foot switch 44 by the operator, the determination of the controller 60 shown in step S20 (see FIG. 6) is YES. In this case, the controller 60 ignores the instruction, in other words, disables the instruction, and continuously executes the abdominal cavity pressure control in steps S1 to S9 shown in FIG. 5 (step S21).

The continuous execution of the abdominal cavity pressure control allows the carbon dioxide gas to be supplied into the abdominal cavity AC, causing the pressure inside the abdominal cavity to increase. After a while, the abdominal cavity pressure reaches the pressure setting displayed on the pressure display 77b or thereabout.

In such a state, the determination in step S3 is YES, so that the controller 60 shifts to the operation in step S1 with the gas-supply interrupted, that is, the first solenoid valve 55 closed.

Thus, as set forth above, the abdominal-cavity pressure control operations allow the pressure inside of the abdominal cavity AC to be kept to the pressure setting or thereabout, which has been set by the operator. Under such a state, the operator specifies the site to be treated inside the abdominal cavity AC while manipulating the rigidscope 21 disposed in the first trocar 14 to observe the affected site. Thereafter, the operator treats the specified site to be treated by using, for example, the electric scalpel 13 inserted inside the abdominal cavity AC via the second trocar 15.

In addition, while the controller 60 repeatedly executes the abdominal-cavity pressure control operations shown in steps S1 to S9 in the abdominal-cavity insufflation mode, when the gas-supply stop button 72 is turned on, the instruction corresponding to the turning-on of the button 72 is sent from the manually operable setting section 63 to the controller 60.

The instruction corresponding g to the turning-on of the button 72 causes the determination in step S9 to be YES, so that the controller 60 controls the first electropneumatic proportional valve 53 and the first solenoid valve 5 to close them (step S14), terminating the abdominal-cavity pressure control operations.

On the other hand, the relief valve R normally keeps in a closed state, and opens depending on the control signal sent from the controller 60 when the pressure value measured by the pressure sensor 57 exceeds the threshold value, for example, the pressure setting displayed on the pressure display 77b by the predetermined value or more. The opening of the relief valve R permits the carbon dioxide gas in the abdominal cavity AC to be relieved in the atmosphere, reducing the pressure inside the abdominal cavity AC to the pressure setting or thereabout.

When the pressure value measured by the pressure sensor 57 exceeds the threshold value by the predetermined pressure or more, the controller 60 can control the excessive pressure indicator 84 to turn on or flash on and off in addition to the control signal sending operation. The turning-on or the flashing of the excessive pressure indicator 84 allows the operator to recognize visually that the pressure inside the abdominal cavity AC exceeds the threshold value by the predetermined pressure or more.

Next, operations of the controller 60 in the lumen insufflation mode will be described hereinafter.

When the operator wants to insufflate the carbon dioxide gas into the lumen BC at first, or the pressure inside the abdominal cavity AC reaches the pressure setting (the determination in step S3 is YES), the operator turns on the lumen select button 83a. The turning-on of the button 83a causes the controller 60 to enter the lumen insufflation mode and to keep the abdominal cavity select button 82a off. The operator depresses switching portion 44a of the foot switch 44.

The manually operable setting section 63 provides the instruction corresponding to the turning-on operation of the button 83a to the controller 60, and the foot switch 44 sends the instruction signal corresponding to the switch-on of the switch portion 44a to the controller 60.

When the instruction corresponding to the turning-on operation of the button 83a is sent to the controller 60, the controller 60 receives the instruction sent thereto to determine that its operation mode is not the abdominal-cavity insufflation mode. In other words, the determination in step S1 is NO.

Thus, in step S10, the controller 60 determines whether the instruction corresponding to the turning-on of the foot switch 44 is sent thereto so as to decide whether its operation mode is the lumen insufflation mode based on the determined result (step S10).

Assuming that no instruction corresponding to the turning-on of the foot switch 44 is sent therefrom to the controller 60, the determination in step S10 will be NO, so that the controller will keep the second electropneumatic proportional valve 54 and the second solenoid valve 56 closed (step S1), returning to the operation in step S1.

Turning now, because the instruction corresponding to the turning-on of the foot switch 44 is sent therefrom to the controller 60, the controller 60 determines its operation mode is the lumen insufflation mode, in other words, the determination in step S10 is YES. Thus, the controller 60 sends the control signal to the second solenoid valve 56 to open it (step S12), and sends the control signal to the second electropneumatic proportional valve 54 to open it (step S13).

These valve controls result in that the carbon dioxide gas, which is reduced in pressure to the predetermined pressure by the pressure reduction unit 52, is supplied into the lumen BC through the second $CO_2$ supply path DC2. Specifically, the carbon dioxide gas with the predetermined pressure is supplied through the second electropneumatic proportional valve 54, the seventh flow channel C7, the second solenoid valve 56, the eighth flow channel C8, the second flow rate sensor 59, the ninth flow channel C9, and the second adapter 41b. Thereafter, the carbon dioxide gas with the predetermined pressure is delivered through the lumen tube 45b and the gas supply channel SC formed inside the flexiblescope 31 into the lumen BC.

Under such a gas supply state, the pressure and the flow-rate of the carbon dioxide gas measured by the supply pressure sensor 51 and the second flow-rate sensor 59, respectively, are sent to the controller 60. The controller 60 calculates the gas remaining volume, the flow-rate of the carbon dioxide gas insufflating into the lumen BC, and the total amount of the carbon dioxide gas stored therein based on the measured values.

The controller 60 executes display control of the panel section 65 to display the calculated gas remaining volume, the flow-rate of the carbon dioxide gas, and the total amount thereof on the gas remaining volume indicators 76, the flow-rate display 80a, and the total volume display 79, respectively.

Specifically in step S13, the controller 60 calculates the difference between the flow-rate measured by second flow-rate sensor 59 and the flow-rate setting displayed on the flow-rate display 80b to determine an opening of the second electropneumatic proportional valve 54 based on the calculated difference.

Subsequently, the controller 60 delivers the control signal to the second electropneumatic proportional valve 54 to open it by the determined opening. This allows the flow-rate of the carbon dioxide gas being insufflated into the lumen BC to be kept to the flow-rate setting or thereabout.

In the meanwhile, the pressure sensor 57 constantly or periodically detects the pressure inside the abdominal cavity AC even while the carbon dioxide gas supply control into the lumen BC is performed. The controller 60 monitors the pressure inside the abdominal cavity AC depending on the pressure value measured by the pressure sensor 57.

It is assumed that the pressure value measured by the pressure sensor 57 exceeds the threshold value, for example, the pressure setting displayed on the pressure display 77b by the predetermined pressure or more during the carbon dioxide gas supply control for the lumen BC. In this assumption, the controller 60 sends the control signals to the second electropneumatic proportional valve 54 and the second solenoid valve 56 to close them so as to interrupt the insufflation of the carbon dioxide gas into the lumen BC. The controller 60 sends the control signal to the relief valve R to open it.

The opening of the relief valve R permits the carbon dioxide gas in the abdominal cavity AC to be released in the atmosphere, reducing the pressure inside the abdominal cavity AC to the pressure setting or thereabout.

After the pressure inside the abdominal cavity AC reaches the pressure setting or thereabout, the controller 60 sends the control signal to the relief valve R to close it. In addition, the controller 60 sends the control signals to the second electropneumatic proportional valve 54 and the second solenoid valve 56 to open them so as to resume the insufflation of the carbon dioxide gas into the lumen BC.

Every time executing the $CO_2$ supply control operations for the lumen BC as set forth above, the controller 60 executes the operation in step S10 to determine whether the instruction is continuously provided from the footswitch 44.

Accordingly, for example, in a case where the operator decides that the pressure inside the body cavity BC has reached a setting settable by the operator, the depressed condition of the switch portion 44a is cancelled. This causes the output of the instruction based on the depression of the switch portion 44a to be stopped, making the determination in step S10 to be NO. The controller 60 controls the second electromagnetic valve 56 and the second electropneumatic proportional valve 54 to close them, thereby stopping the supply of carbon dioxide gas into the body cavity BC (step S11), returning to the operation in step S1.

Incidentally, in the embodiment, the operations of the controller 60 in steps S2 to S8, the first electropneumatic proportional valve 53, and the first solenoid valve 55 correspond to an example of means for regulating a pressure of the predetermined gas to a first pressure according to the present invention. The foot switch 44 corresponds to an example of sending means according to the embodiment. The operation of the controller 60 in step S10 corresponds to an example of determining means according to the present invention. The operations of the controller 60 in steps S12 to S13, the second electropneumatic proportional valve 54, and the second solenoid valve 56 correspond to an example of means for regulating the pressure of the predetermined gas to a second pressure.

As set forth above, in the embodiment, when the abdominal-cavity insufflation mode is selected upon operation of the abdominal cavity select button 82a, the carbon dioxide gas is supplied into the abdominal cavity AC through the first $CO_2$ supply path DC1 without being delivered to the second $CO_2$ supply path DC2. Specifically, even if the operator depresses the switch portion 44a of the foot switch 44 to turn on in the abdominal-cavity insufflation mode, the controller 60 can ignore the instruction corresponding to the switch-on of the foot switch 44 with the second electropneumatic proportional valve 54 and the second electromagnetic valve 56 kept closed. This makes it possible to prevent the carbon dioxide gas from being insufflated into the lumen BC in the abdominal-cavity insufflation mode.

On the other hand, when the lumen insufflation mode is selected upon operation of the lumen select button 83a, the carbon dioxide gas is supplied into the lumen BC through the second $CO_2$ supply path DC2 without being delivered to the first $CO_2$ supply path DC1. Specifically, in the lumen insufflation mode, the first electropneumatic proportional valve 53 and the first electromagnetic valve 55 are kept closed, making it possible to prevent the carbon dioxide gas from being insufflated into the abdominal cavity AC in the lumen insufflation mode.

As described above, in the embodiment, turning on any one of the select switches 82a and 83a allows selecting any one of the operations (steps) to insufflate the carbon dioxide gas into the abdominal cavity AC and those to insufflate it into the lumen BC. This makes it possible to prevent the carbon dioxide gas from being insufflated into both the abdominal cavity AC and the lumen BC, thereby keeping the pressure inside the abdominal cavity AC and that inside the lumen BC stable individually.

In addition, in the embodiment, the treatment tool channel 34a formed inside the adapter 43 and communicated with the treatment tool insertion opening 38 is larger than the gas and water supply channel in inner diameter, and is shorter than the gas and water supply channel in axial length. Moreover, the treatment tool channel 34a and the gas supply channel SC formed inside the flexiblescope 31 causes the carbon dioxide gas to be delivered toward the lumen BC.

This configuration of the treatment tool channel 34a permits pressure generated when the carbon dioxide gas is insufflated to decrease more in the treatment tool channel 34a than in the gas and water supply channel. This makes it possible to supply the carbon dioxide gas into the lumen BC smoothly.

Moreover, in the embodiment, when the carbon dioxide gas is supplied into the lumen BC, turning on and off the switch portion 44a of the foot switch 44 by the operator allow switching between insufflation of the carbon dioxide gas into the lumen BC and interruption thereof. In other words, it is possible for the operator to operate the foot switch 44 to supply the carbon dioxide gas into the lumen BC only when the operator decides to require the supply of the carbon dioxide gas thereinto without continually supplying it. This makes it possible to reliably prevent wasteful dissipation of the carbon dioxide stored in the $CO_2$ bottle 42 in liquid during the insufflation of the carbon dioxide gas into the lumen BC.

Furthermore, in the embodiment, the adapter 43 serves as a coupler between the gas delivery channel SC as part of the second $CO_2$ supply path DC2 and the lumen tube 45b as part thereof. In addition, the adapter 43 is arranged at a position closer to the insertion section 34 than the gas and water supply switch 35a through which the through hole is formed. This configuration provides the second $CO_2$ supply path DC2 extending from the gas supply apparatus 41 into the lumen BC through the tube 45b, the hollow space 43d of the adapter 43, the instrument tool channel 34a, and the gas delivery channel SC without passing through the through hole formed in the switch 35a.

Accordingly, when supplying the carbon dioxide gas into the lumen BC through the flexiblescope 31, it is possible to reliably prevent part of the carbon dioxide gas from being leaked out of the through hole formed in the switch 35a. This makes it possible to prevent wasteful dissipation of the carbon dioxide stored in the $CO_2$ bottle 42 in liquid further reliably during the insufflation of the carbon dioxide gas into the lumen BC.

In view of this, in the embodiment, the operator is able to perform the operations to supply the carbon dioxide gas into the lumen BC and to interrupt the supply thereof by the operations to depress the switch portion 44a of the foot switch 44 and release it without opening and closing the through hole in the switch 35a.

The configuration of the embodiment therefore makes it possible to reliably prevent part of the carbon dioxide gas from being leaked out of the through hole formed in the switch 35a while keeping high the operability of the second endoscope system 3 for supplying the carbon dioxide gas and interrupting it in the lumen insufflation mode.

In addition, in the embodiment, the slit 43c is formed on the adapter 43 with the tube coupling portion 43a to which the lumen tube 45b is coupled. This configuration allows an instrument tool to be inserted through the slit 43c into the lumen BC with the carbon dioxide gas being supplied thereinto through the adapter 43.

Incidentally, in the embodiment, the foot switch cable 44b extending from the foot switch 44 is electrically connected to the gas supply apparatus 41, but it can be electrically connected to the system controller 5. This modification allows the system controller 5 to execute the gas delivery control operations independently or in cooperation with the controller 60.

In addition, switches functionally associated with the gas supply start button 72 and gas supply stop button 73 provided on the gas supply apparatus 41 may be attached to the foot switch 44 in addition to the switch portion 44a. Specifically, at least one switch for enabling an instruction to start insufflation of the carbon dioxide gas and that to stop it may be attached to the foot switch 44 in addition to the switch portion 44*a*.

This modification allows an operator, who manipulates the flexiblescope 31 and is in charge of executing a treatment, to depress the switches attached to the footswitch 44 and functionally associated with the buttons 72 and 73, respectively. This makes it possible for the treatment operator to easily give the controller 60 instructions for starting insufflation of the carbon dioxide gas and for stopping it without trouble of another operator, such as a nurse or the like. In addition, in place of the footswitch 44, a hand switch may be detachably mounted on, for instance, the manipulator 35 of the flexiblescope 31. This enables an operator, who manipulates the flexiblescope 31 and is in charge of executing a treatment, to easily give the controller 60 instructions for starting insufflation of the carbon dioxide gas and for stopping it.

Figure 5:
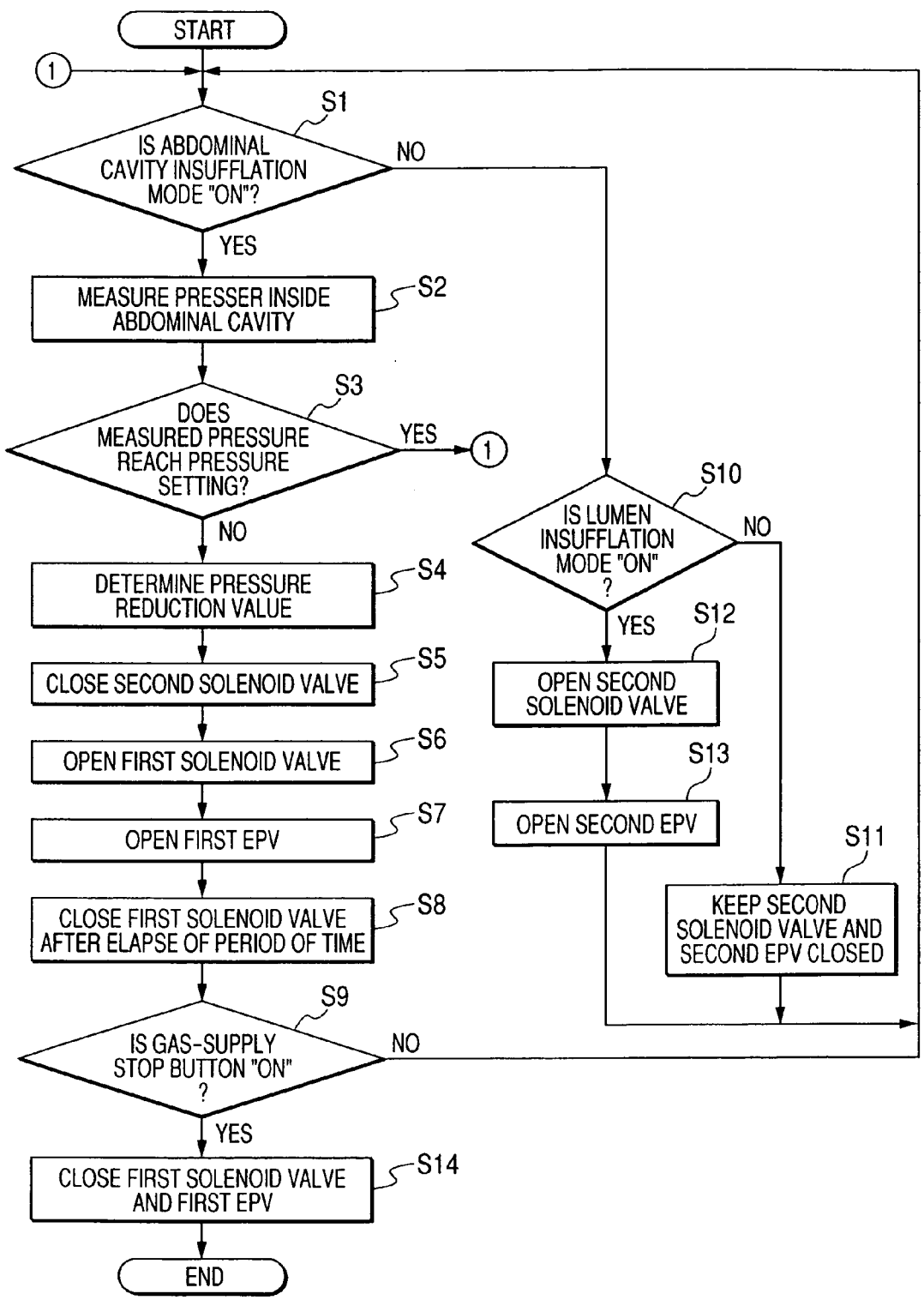
FIG. 5 is a flowchart schematically illustrating an example of control operations of a controller illustrated in FIG. 2.
Figure 6:
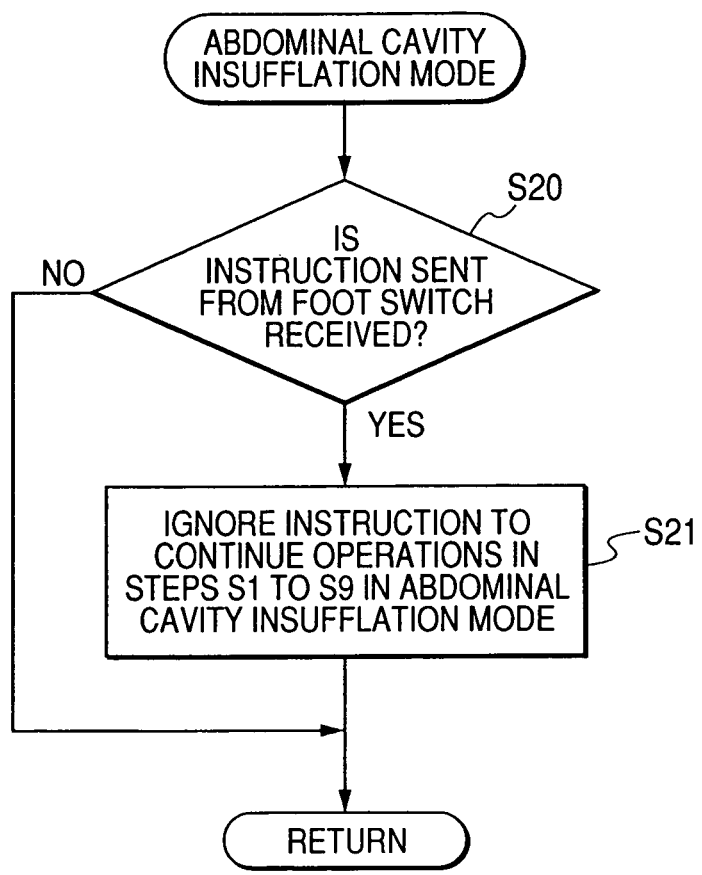
FIG. 6 is a flowchart schematically illustrating an example of part of the control operations of the controller shown in FIG. 5.

Incidentally, the insufflation control operations of the controller 60 of the gas supply apparatus 41 has been described based on FIGS. 5 and 6, the present invention is not limited to such operations. Specifically, the controller 60 can execute insufflation control operations described hereinafter as a modification.

In the modification, the abdominal cavity select button 82*a* is configured to send to the controller 60 an instruction to make it execute operations for supplying the carbon dioxide gas into the abdominal cavity AC. In other words, turning on and off of the abdominal cavity select button 82*a* allows the abdominal-cavity insufflation mode of the controller 60 to be switched between the on state and off state. When the abdominal-cavity insufflation mode is switched on, the controller 60 turns on the abdominal-cavity insufflation mode indicator 82*b*.

On the other hand, the lumen select button 83*a* is configured to send to the controller 60 an instruction to make it execute operations for supplying the carbon dioxide gas into the lumen BC. In other words, turning on and off of the lumen select button 83*a* permits the lumen insufflation mode of the controller 60 to be switched between the on state and off state. When the lumen insufflation mode is switched on, the controller 60 turns on the lumen insufflation mode indicator 83*b*.

In addition, in the modification, the abdominal cavity select button 82*a* and the lumen select button 83*a* are configured to allow the operator to operate them independently from each other.

Specifically, when executing only insufflation of the carbon dioxide gas into the abdominal cavity AC, the operator operates or keeps the abdominal cavity select button 82*a* on, and operates or keeps the lumen select button 83*a* off. The on state of the button 82*a* turns on the abdominal-cavity insufflation mode of the controller 60, and the off state of the button 83*a* turns off the lumen insufflation mode thereof.

Similarly, when executing only insufflation of the carbon dioxide gas into the lumen BC, the operator operates or keeps the lumen select button 83*a* on, and operates or keeps the abdominal cavity select button 82*a* off. The on state of the button 83*a* turns on the lumen insufflation mode of the controller 60, and the off state of the button 82*a* turns off the abdominal-cavity insufflation mode thereof.

Next, an example of control operations of the controller 60 when both the buttons 82*a* and 83*a* are in on state will be described hereinafter with reference to FIG. 7.

Figure 7:
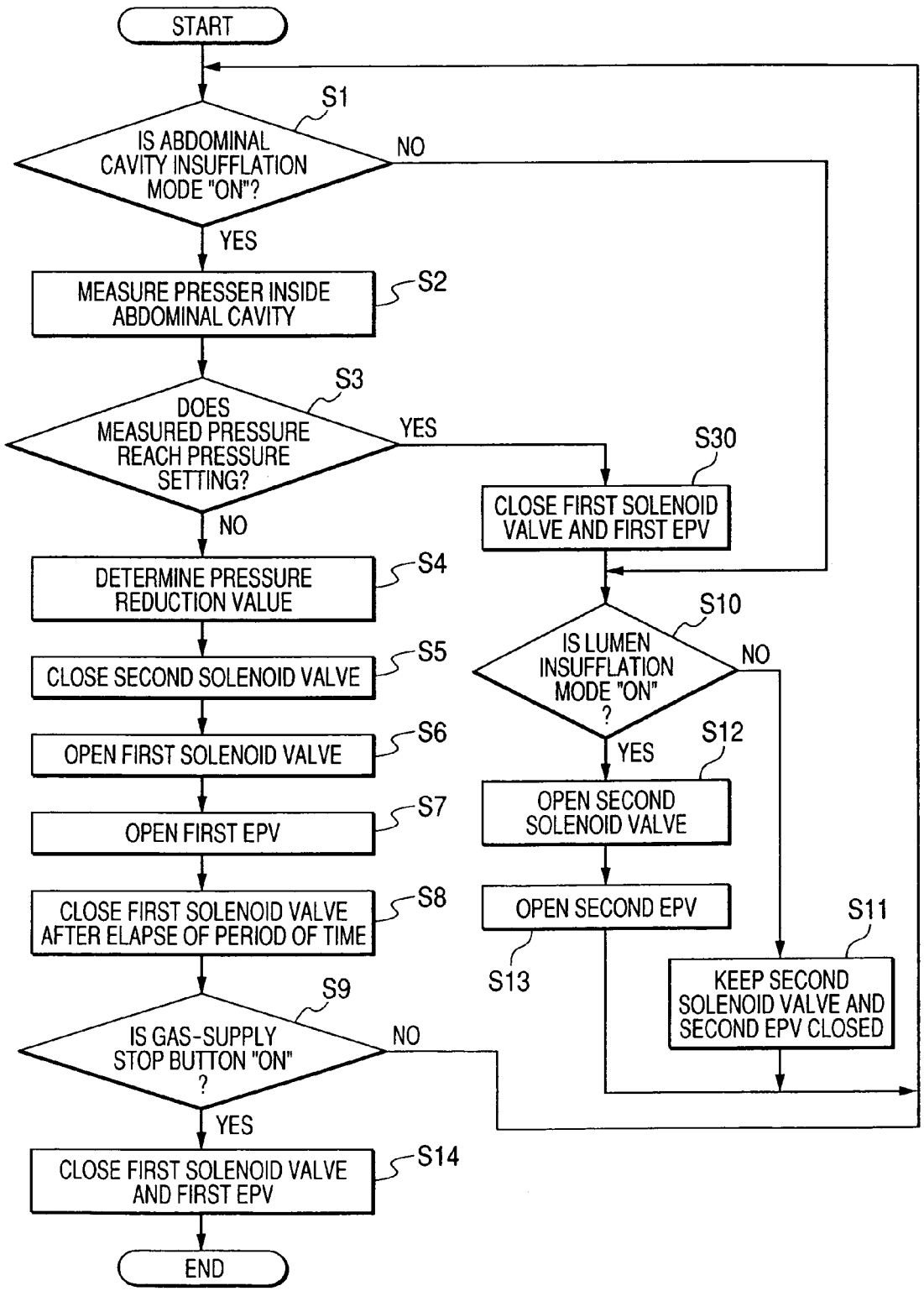
FIG. 7 is a flowchart schematically illustrating modification of the control operations of the controller illustrated in FIG. 2.

While both the buttons 82*a* and 83*a* are in on state, turning on of the gas-supply start button 72 by the operator causes the controller 60 to start to supply the carbon dioxide gas into the abdominal cavity AC shown in steps S1 to S9 of FIG. 7 (FIG. 5). During the insufflation control of the controller 60 for the abdominal cavity AC, the second solenoid valve 56 is kept closed. In addition, even if the operator depresses the switch portion 44*a* of the foot switch 44 to turn on during the insufflation control of the controller 60 for the abdominal cavity AC, the controller 60 ignores the instruction corresponding to the switch-on of the foot switch 44 (see step S21 in FIG. 6). This allows the insufflation of the carbon dioxide gas through the first adapter 41*a* irrespective of the switching of the foot switch 44 to prevent the carbon dioxide gas from being insufflated through the second adapter 41*b*.

When the abdominal cavity pressure reaches the pressure setting displayed on the pressure display 77*b* or thereabout, the determination in step S3 is YES, so that the controller 60 sends the control signals to the first solenoid valve 55 and the first electropneumatic proportional valve 53 to close them, respectively (step S30). As a result, when the insufflation of the carbon dioxide gas through the first adapter 41*a* is stopped, the controller 60 shifts to the operation in step S10.

Specifically, it is not until the insufflation of the carbon dioxide gas is stopped through the first adapter 41*a* that the controller 60 controls the second solenoid valve 56 and the second electropneumatic valve 54 to close them in response to the turning on of the switch portion 44*a* of the foot switch 44. This causes start of the insufflation of the carbon dioxide gas into the lumen BC.

While the carbon dioxide gas is supplied into the lumen BC, the pressure sensor 57 constantly or periodically detects the pressure inside the abdominal cavity AC. The controller 60 monitors the pressure inside the abdominal cavity AC depending on the pressure value measured by the pressure sensor 57.

It is assumed that the pressure value measured by the pressure sensor 57 falls down from the pressure setting displayed on the pressure display 77*b* by a predetermined pressure or more during the insufflation of the carbon dioxide gas into the lumen BC. In this assumption, the controller 60 sends the control signals to the second electropneumatic proportional valve 54 and the second solenoid valve 56 to close them so as to interrupt the insufflation of the carbon dioxide gas into the lumen BC (see step S5). Next, the controller 60 sends the control signals to the first electropneumatic proportional valve 53 and the first solenoid valve 55 to open them. Specifically, the controller 60 executes the operations in steps S3 to S8 repeatedly to insufflate the carbon dioxide gas into the abdominal cavity AC until the pressure inside the abdominal cavity, which is measured by the pressure sensor 57, reaches the pressure setting or thereabout. After the pressure inside the abdominal cavity AC reaches the pressure setting, the controller 60 shifts to the operation in step S12 to resume insufflation of the carbon dioxide gas into the lumen BC.

On the other hand, it is assumed that the pressure value measured by the pressure sensor 57 exceeds the threshold value, for example, the pressure setting displayed on the pressure display 77*b* by the predetermined pressure or more during the insufflation of the carbon dioxide gas into the lumen BC. In this assumption, the controller 60 sends the control signals to the second electropneumatic proportional valve 54 and the second solenoid valve 56 to close them so as to interrupt the insufflation of the carbon dioxide gas into the lumen BC. The controller 60 sends the control signal to the relief valve R to open it.

The opening of the relief valve R permits the carbon dioxide gas in the abdominal cavity AC to be released in the atmosphere, reducing the pressure inside the abdominal cavity AC to the pressure setting or thereabout.

After the pressure inside the abdominal cavity AC reaches the pressure setting or thereabout, the controller 60 sends the control signal to the relief valve R to close it. In addition, the controller 60 sends the control signals to the second electropneumatic proportional valve 54 and the second solenoid valve 56 to open them so as to resume the insufflation of the carbon dioxide gas into the lumen BC.

As described above, in the modification of the insufflation control operations, when the gas-supply start button 72 is turned on while both switches 82a and 83a are on states, the carbon dioxide gas is supplied into the abdominal cavity AC through the first $CO_2$ supply path DC1 without being delivered to the second $CO_2$ supply path DC2.

Specifically, even if the operator depresses the switch portion 44a of the foot switch 44 to turn on while the gas-supply start button 72 is turned on, the controller 60 keeps the second electropneumatic proportional valve 54 and the second electromagnetic valve 56 closed. This makes it possible to prevent the carbon dioxide gas from being insufflated into the lumen BC in the abdominal-cavity insufflation mode.

On the other hand, while the gas-supply start button 72 is off state, and both switches 82a and 83a are on states, the turning-on of the foot switch 44 allows the carbon dioxide gas to be supplied into the lumen BC through the second path DC2 without the gas being delivered to the first path DC1.

Specifically, while the instruction corresponding to the turning-on of the foot switch 44 is continuously therefrom to the controller 60, the first electropneumatic proportional valve 53 and the first electromagnetic valve 55 are kept closed, making it possible to prevent the carbon dioxide gas from being insufflated into the abdominal cavity AC.

That is, in the modification illustrated in FIG. 7, it is possible to select any one of the operations (steps) to insufflate the carbon dioxide gas into the abdominal cavity AC and those to insufflate it into the lumen BC depending on the pressure value measured by the pressure sensor 57 and the instruction sent from the foot switch 44.

This prevents the carbon dioxide gas from being supplied into both the abdominal cavity AC and the lumen BC, thereby keeping the pressure inside the abdominal cavity AC and that inside the lumen BC stable individually.

Insufflation control operations of the controller 60 of the gas supply apparatus 41 will be described in more detail with reference to FIG. 8.

Specifically, with the power switch 71 turned on upon operation of the operator, the controller 60 starts to execute insufflation control operations based on the turning-on of the power switch 71.

Figure 8:
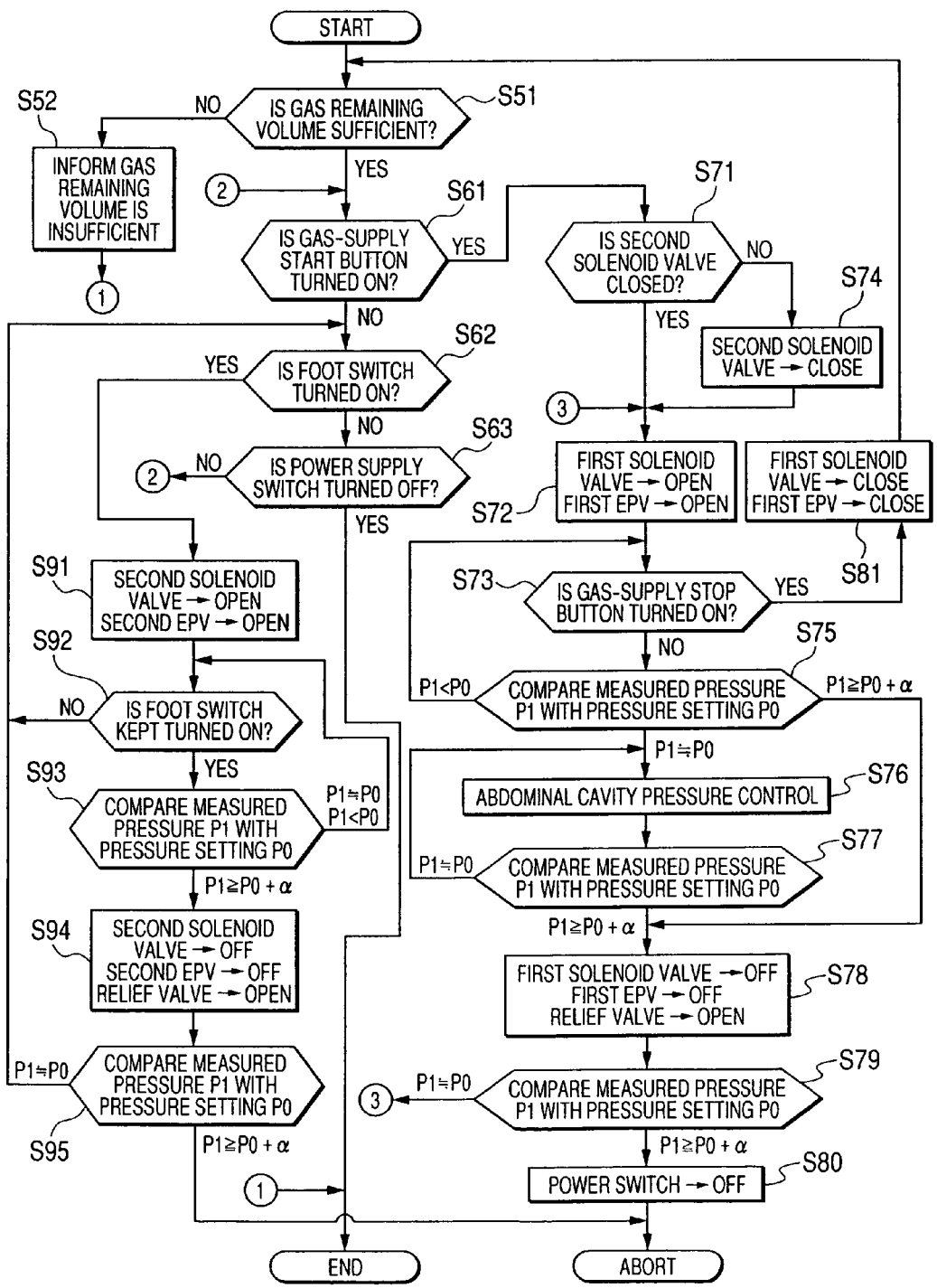
FIG. 8 is a flowchart illustrating in detail control operations of the controller shown in FIG. 2.

First, as shown in FIG. 8, the controller 60 checks the gas remaining volume in the $CO_2$ bottle 42 to determine whether the checked volume is sufficient in step S51. When it is determined that the checked volume is insufficient (the determination in step S51 is NO), the controller 60 shifts to step S52 to inform the operator and the like of the occurrence of shortage in the gas remaining volume in the $CO_2$ bottle 42, terminating the insufflation control operations In contrast, when it is determined that the checked volume is sufficient (the determination in step S51 is YES), the controller 60 determines:

whether the instruction corresponding to the turning-on operation of the gas-supply start button 72 is sent from the manually operable setting section 63 in step S61;

whether the instruction corresponding to the turning-on operation of the foot switch 44 is sent therefrom in step S62; and whether the instruction corresponding to the turning-off operation of the power supply switch 71 is sent therefrom in step S63.

When no instructions are sent to the controller 60 (each of the determinations in steps S61 to S63 is NO), the controller 60 waits until any one of the instructions is sent to the controller 60.

When the instruction corresponding to the turning-on operation of the gas-supply start button 72 is sent from the manually operable setting section 63 (the determination in step S61 is YES), the controller 60 shifts to step S71. In step S71, the controller 60 determines whether the second solenoid valve 56 is closed. When it is determined that the second solenoid valve 56 is closed (the determination in step S71 is YES), the controller 60 shifts to step S72 to send the control signals to the first electropneumatic proportional valve 53 and the first electromagnetic valve 55 to open them. The opening of each of the valves 53 and 55 allows start of insufflation of the carbon dioxide gas into the abdominal cavity AC. After the gas insufflation start operation in step S72, the controller 60 shifts to step S73.

On the other hand, when it is determined that the second solenoid valve 56 is opened (the determination in step S71 is YES), the controller 60 shifts to step S74 to close the second solenoid valve 56, shifting to step S72. The closing of the second solenoid valve in step S74 allows the insufflation of the carbon dioxide gas to be interrupted.

In step S73, the controller 60 determines whether the instruction corresponding to the turning-on operation of the gas-supply stop button 73 is sent from the manually operable setting section 63. When it is determined that no instruction corresponding to the turning-on operation of the gas-supply stop button 73 is sent from the manually operable setting section 63 (the determination in step S73 is NO), the controller 60 shifts to step S75. In step S75, the controller 60 compares the measured pressure (P1) outputted from the pressure sensor 57 with the pressure setting (P0) inside the abdominal cavity AC.

In step S75, when it is determined that the measured pressure P1 is nearly equal to the pressure setting P0, which is represented as "P1≈P0", the controller 60 shifts to step S76 to execute the abdominal-cavity pressure control operations in steps S3 to S8 to keep the pressure inside the abdominal cavity AC to the pressure setting or thereabout.

On the other hand, in step S75, when it is determined that the measured pressure P1 is higher than the pressure setting P0 by the predetermined pressure ($\alpha$) or more, which is represented as "P1≥P0+$\alpha$", the controller 60 shifts to step S78. In step S78, the controller 60 sends the control signals to the first electropneumatic proportional valve 53 and the first solenoid valve 55 to close them, respectively, and sends the control signal to the relief valve R to open it.

After a predetermined period of time has elapsed from the operation in step S78, the controller 60 shifts to step S79 to compare the measured pressure (P1) outputted from the pressure sensor 57 with the pressure setting (P0) inside the abdominal cavity AC.

The opening of the relief valve R in step S78 permits the carbon dioxide gas in the abdominal cavity AC to be released in the atmosphere, reducing the pressure inside the abdominal cavity AC to the pressure setting or thereabout.

Specifically, after the predetermined period of time has elapsed from the operation in step S78, when it is determined that at the measured pressure P1 is nearly equal to the pressure setting P0 (P1≈P0) in step S79, the controller 60 shifts to step S72 to execute the abdominal-cavity pressure control operations in steps S3 to S8 to keep the pressure inside the abdominal cavity AC to the pressure setting or thereabout.

On the other hand, after the predetermined period of time has elapsed from the operation in step S78, when it is determined that the measured pressure P1 is higher than the pressure setting P0 by the predetermined pressure (α) or more (P1≥P0+α) in step S79, the controller 60 shifts to step S80. In step S80, the controller 60 forcibly turns off the power switch 71 to abort the insufflation control operations.

Incidentally, in step S75, until the measured pressure (P1) outputted from the pressure sensor 57 reaches the pressure setting (P0), in other words, while the measured pressure (P1)<the pressure setting (P0), the controller 60 shifts to step S73 to continuously execute the operations in steps S73 and S74 in, for example, a cycle. This results in that the carbon dioxide gas is continuously supplied into the abdominal cavity AC.

Turn to step S73, when it is determined that the instruction corresponding to the turning-on operation of the gas-supply stop button 73 is sent from the manually operable setting section 63 (the determination in step S73 is YES), the controller 60 shifts to step S81. In step S81, the controller 60 sends the control signals to the first electropneumatic proportional valve 53 and the first solenoid valve 55 to close them, respectively, causing the insufflation of the carbon dioxide gas into the abdominal cavity AC to be stopped. After that, the controller 60 shifts to step S61.

Turn to step S62, when it is determined that the instruction corresponding to the turning-on operation of the foot switch 44 is sent therefrom (the determination in step S62 is YES), the controller 60 shifts to step S91. In step S91, the controller 60 sends the control signals to the second electropneumatic proportional valve 54 and the second solenoid valve 56 to open them, respectively. The opening of each of the valves 54 and 56 allows start of insufflation of the carbon dioxide gas into the lumen BC. After the gas insufflation start operation in step S91, the controller 60 shifts to step S92. In step S92, the controller 60 determines whether the instruction corresponding to the turning-on operation of the foot switch 44 has been sent therefrom.

In step S92, when it is determined that the instruction corresponding to the turning-on operation of the foot switch 44 has been sent therefrom (the determination in step S92 is YES), the controller 60 shifts to step S93 to compare the measured pressure (P1) outputted from the pressure sensor 57 with the pressure setting (P0) inside the abdominal cavity AC.

In step S93, when it is determined that the measured pressure P1 is higher than the pressure setting P0 by the predetermined pressure (α) or more (P1≥P0+α), the controller 60 shifts to step S94.

In step S94, the controller 60 sends the control signals to the second electropneumatic proportional valve 54 and the second solenoid valve 56 to close them, respectively, and sends the control signal to the relief valve R to open it.

The opening of the relief valve R in step S94 permits the carbon dioxide gas in the abdominal cavity AC to be released in the atmosphere, reducing the pressure inside the abdominal cavity AC to the pressure setting or thereabout.

After a predetermined period of time has elapsed from the operation in step S94, the controller 60 shifts to step S95 to compare the measured pressure (P1) outputted from the pressure sensor 57 with the pressure setting (P0) inside the abdominal cavity AC.

Specifically, after the predetermined period of time has elapsed from the operation in step S94, when it is determined that at the measured pressure P1 is nearly equal to the pressure setting P0 (P1≈P0) in step S95, the controller 60 shifts to step S62.

On the other hand, after the predetermined period of time has elapsed from the operation in step S94, when it is determined that the measured pressure P1 is higher than the pressure setting P0 by the predetermined pressure (α) or more (P1≥P0+α) in step S94, the controller 60 shifts to step S80. In step S80, the controller 60 forcibly turns off the power switch 71 to abort the insufflation control operations.

On the other hand, in step S92, when the controller 60 determines that the instruction corresponding to the turning-on operation of the foot switch 44 is not detected (the determination in step S92 is NO), the controller 60 shifts to step S62. In step S92, until the measured pressure (P1) outputted from the pressure sensor 57 reaches the pressure setting (P0), in other words, while the measured pressure (P1)<the pressure setting (P0), the controller 60 shifts to step S92 to continuously execute the operations in steps S92 and S93 in, for example, a cycle. This results in that the carbon dioxide gas is continuously supplied into the lumen BC.

As described above, when the gas-supply start button 72 is turned on while both switches 82a and 83a are on states (see the determination in step S61 is YES), the carbon dioxide gas is supplied into the abdominal cavity AC through the first path DC1 without being delivered to the second path DC2 (see steps S71 to 79).

In addition, while the gas-supply start button 72 is off state, and both switches 82a and 83a are on states (see the determination in step S61 is NO), the turning-on of the foot switch 44 allows the carbon dioxide gas to be supplied into the lumen BC through the second path DC2 without the gas being delivered to the first path DC1 (see steps S62, and S91 to S95).

Incidentally, insufflation control operations of the controller 60 of the gas supply apparatus 41 according to the present invention are not limited to those illustrated in FIGS. 5 to 8. Specifically, another modification of the insufflation control operations of the controller 60 allows insufflation of the carbon dioxide gas through both the first and second adapter 41a and 41b.

Another modification of the insufflation control operations of the controller 60 for insufflating the carbon dioxide gas through both the first and second adapter 41a and 41b will be described hereinafter with reference to FIG. 9. Incidentally, description is made with attention focused on points different from the operations that have already been described above with reference to FIGS. 5 and 7.

Figure 9:
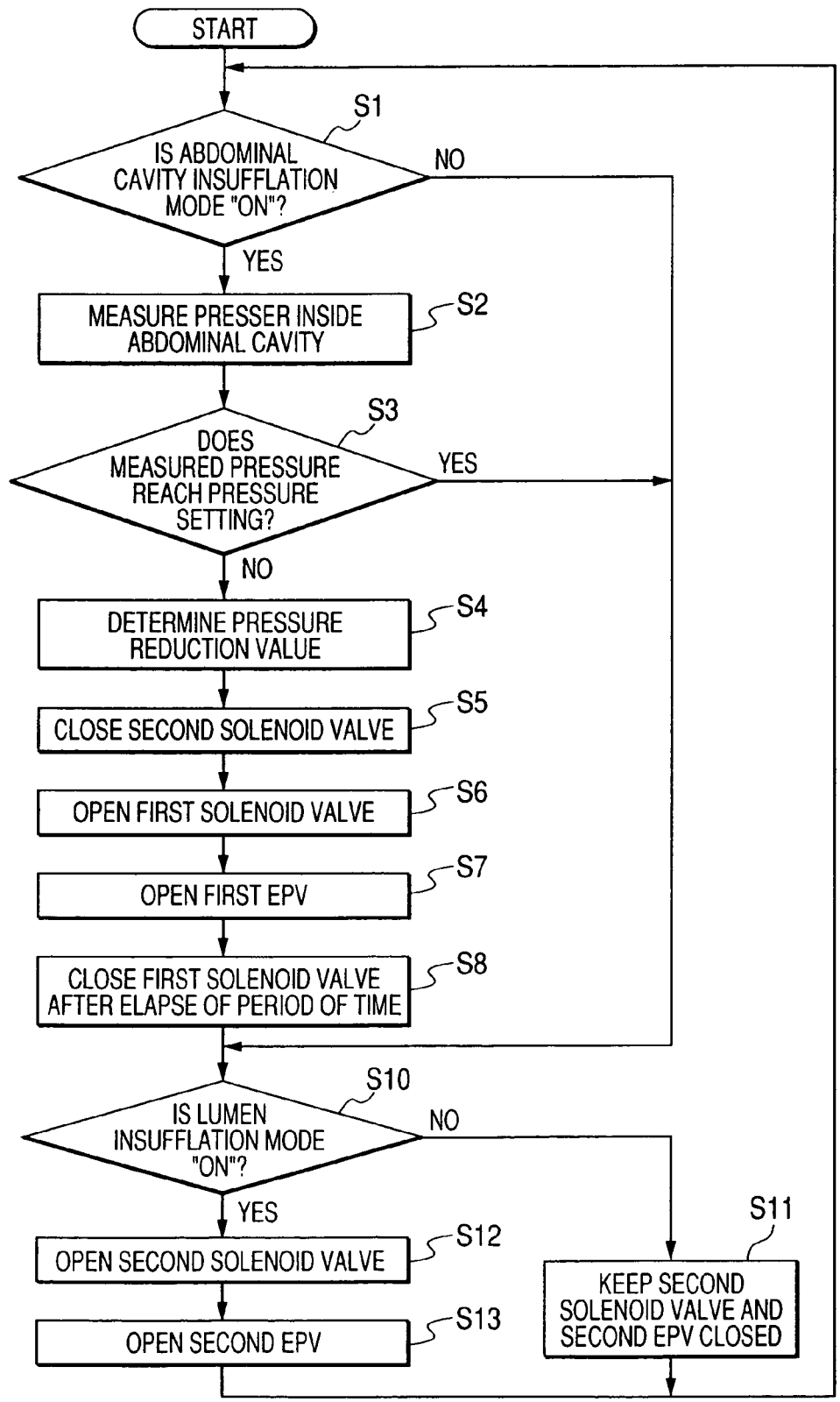
FIG. 9 is a view schematically illustrating another modification of the control operations of the controller illustrated in FIG. 2.

Referring to FIG. 9, the modification of the insufflation control operations of the controller 60 when both the buttons 82a and 83a are in on state will be described hereinafter.

Turning on of the gas-supply start button 72 by the operator causes the controller 60 to start to supply the carbon dioxide gas into the abdominal cavity AC shown in steps S1 to S4 and S6 to S8 of FIG. 9 (FIGS. 5 and 7). When no instruction corresponding to the turning-on of the foot switch 44 is sent therefrom in step S10 (the determination in step S10 is NO), the controller 60 proceeds to step S11 to close the second electromagnetic valve 56, returning to step S1.

In contrast, when the instruction corresponding to the turning-on of the foot switch 44 is sent therefrom in step S10 (the determination in step S10 is YES), the controller 60 sends the control signals to the second electromagnetic valve 56 and the second electropneumatic proportional valve 54 to open them, respectively, in steps S12 and S13. After that, the controller 60 shifts to step S1.

As a result, the insufflation of the carbon dioxide gas into the abdominal cavity AC and that of the carbon dioxide gas into the lumen BC are executed independently from each other.

Specifically, when insufflating the carbon dioxide gas into the abdominal cavity AC, the controller 60 performs alternately the operations to supply the carbon dioxide gas into the abdominal cavity AC and those to interrupt the supply thereof. More specifically, the controller 60 detects the pressure inside the abdominal cavity AC based on the measured value of the pressure sensor 57 to monitor the difference between the pressure inside the abdominal cavity and the pressure setting previously set by, for example, the operator. Thus, the controller 60 adjusts the opening of the first electropneumatic proportional valve 53 based on the monitored result, thereby controlling the pressure and the flow-rate of the carbon dioxide gas insufflated into the abdominal cavity AC.

While the carbon dioxide gas is insufflated into the lumen BC, the pressure sensor 57 detects the pressure inside the abdominal cavity AC at timing when the gas insufflated into the abdominal cavity AC is interrupted so that the controller 60 monitors the pressure inside the abdominal cavity AC.

When the measured pressure inside the abdominal cavity is lower than the pressure setting by a predetermined value or more, the controller 60 controls the opening of the first electropneumatic proportional valve 53 to continuously supply the carbon dioxide gas into the abdominal cavity until the pressure inside the abdominal cavity AC reaches the pressure setting or thereabout.

In contrast, when the measured pressure inside the abdominal cavity is higher than the pressure setting by a predetermined value or more, the controller 60 closes the first solenoid valve 55 and the first electropneumatic proportional valve 53 to interrupt the insufflation of the gas into the abdominal cavity AC and to open the relief valve R.

These controls of the valves 53, 55, and R allow the carbon dioxide gas in the abdominal cavity AC to be relieved in the atmosphere, reducing the pressure inside the abdominal cavity AC to the pressure setting or thereabout.

As described above, the controller 60 controls the first electromagnetic valve 55 and the first electropneumatic proportional valve 53 depending on the measured value of the pressure sensor 57, which allows the pressure inside the abdominal cavity AC to be keep it stable.

Incidentally, in the embodiment and its modifications, the controller 60 carries out the insufflation control operations shown in FIGS. 5 to 9, but the system controller 5 can execute them.

In addition, in the embodiment and its modifications, the rigidscope and the flexiblescope are used as observation devices for observing the inside of a specimen, but the present invention is not limited to the structure. Specifically, other types of endoscopes, such as a wireless capsule endoscope or the like, or other observation devices except for endoscopes, each of which is configured to be inserted into the inside of a specimen, can be used for observing the inside of the specimen.

Furthermore, it should be noted that the term "body cavity" means not only a cavity that originally exists in the body of a specimen, but also a cavity (space) to be artificially formed in the body of a specimen with medical instruments.

For example, the term "body cavity" according to the specification includes, as the former means, an abdominal cavity, a lumen including upper alimentary tracts (esophagus, stomach, or the like), lower alimentary tracts (large intestine, small intestine, or the like), a bladder, and a uterus.

In addition, the term "body cavity" according to the specification includes, as the later means, a cavity to secure the field of an endoscope during surgery, such as subcutaneous cavity and the like.

While there has been described what is at present considered to be the embodiment and modifications of the invention, it will be understood that various modifications which are not described yet may be made therein, and it is intended to cover in the appended claims all such modifications as fall within the true spirit and scope of the invention.

What is claimed is:

1. A gas supply system for supplying predetermined gas to a first body cavity of a patient through a first delivery member and to a second body cavity of the patient through a second delivery member, the gas supply system comprising:
    a pressure regulator coupled to the first and second delivery members and configured to regulate a pressure of the predetermined gas to a first pressure and a second pressure, the first pressure being suitable for the first body cavity, the second pressure being suitable for the second body cavity, the pressure regulator allowing the predetermined gas with its pressure regulated to be supplied to both the first and second delivery members;
    a first operation switch that switches, when operated by an operator, a first mode and a second mode, in the first mode, the gas supply system being configured such that the predetermined gas with its pressure regulated is only supplied to the first delivery member, in the second mode, the gas supply system being configured such that the predetermined gas with its pressure regulated is only supplied to the second delivery member; and
    a controller electrically connected to the pressure regulator and the first operation switch and operative to control the pressure regulator according to one of the first and second modes switched by the first operation switch.

2. A gas supply system according to claim 1, wherein the controller is operative to:
    execute a first control to control the pressure regulator in the first mode so that the predetermined gas is only supplied to the first delivery member and the pressure thereof is regulated to the first pressure to raise a pressure inside the first body cavity up to a predetermined pressure setting or thereabout; and
    execute a second control to control the pressure regulator in the second mode so that the predetermined gas is switched to the second delivery member and the pressure thereof is switched to the second pressure.

3. A gas supply system according to claim 2, further comprising a second operation switch operable by the operator, wherein the controller is configured to execute the second control in the second mode only when an instruction is sent from the second operation switch operated by the operator.

4. A gas supply system according to claim 3, wherein, when the instruction is sent from the second operation switch while executing the first control, the controller ignores the instruction and continuously executes the first control.

5. A gas supply apparatus according to claim 4, wherein the operation switch is a foot switch operable with the operator's foot.

6. A gas supply apparatus according to claim 1, wherein the pressure regulator comprises:
    a first electropneumatic regulator provided in the first delivery member and electrically connected to the controller;
    a first opening and closing valve provided in the first delivery member at downstream of the first electropneumatic regulator and electrically connected to the controller;
    a second electropneumatic regulator provided in the second delivery member and electrically connected to the controller; and
    a second opening and closing valve provided in the second delivery member at downstream of the first electropneumatic regulator and electrically connected to the controller;

7. A gas supply apparatus according to claim 6, further comprising a second operation switch operable by the operator, wherein the controller is operative to:
- execute a first control to:
  - close the second opening and closing valve and open the first opening and closing valve so that the predetermined gas is only supplied to the first delivery member, and
  - control the first electropneumatic regulator so that the pressure of the predetermined gas supplied to the first delivery member is regulated to the first pressure to raise a pressure inside the first body cavity up to a predetermined pressure setting or thereabout; and
- execute a second control to:
  - when the instruction is sent from the second operation switch after the pressure inside the first body cavity has been raised up to the predetermined pressure setting or thereabout, close the first opening and closing valve and open the second opening and closing valve so that the predetermined gas is switched to the second delivery member, and
  - control the second electropneumatic regulator so that the pressure of the predetermined gas is switched to the second pressure.

8. A gas supply apparatus according to claim 7, further comprising a pressure sensor provided in the first delivery member and electrically connected to the controller, the pressure sensor measuring the pressure inside the first body cavity,
  wherein the controller monitors the pressure inside the first body cavity measured by the pressure sensor while executing the first control to determine whether the pressure inside the first body cavity rises up to the predetermined pressure setting or thereabout based on the monitored result.

9. A gas supply apparatus according to claim 1, wherein the controller is operative to:
  - execute a first control to control the pressure regulator so that the predetermined gas is supplied to the first delivery member and the pressure thereof is regulated to the first pressure to raise a pressure inside the first body cavity up to a predetermined pressure setting or thereabout; and
  - execute a second control, independently from the first control, to control the pressure regulator so that the predetermined gas is switched to the second delivery member and the pressure thereof is switched to the second pressure when the instruction is sent from the operation switch after the pressure inside the first body cavity has been raised up to the predetermined pressure setting or thereabout.

10. A gas supply apparatus according to claim 1, wherein the first body cavity is an abdominal cavity inside the patient, the second body cavity is a lumen inside the patient, and the second delivery member includes;
  - a guide member through which the predetermined gas with its pressure regulated to the second pressure is guided; and
  - a gas delivery channel formed in an observation device and communicably coupled to a portion of the guide member, the observation device having an insert portion to be inserted into the second body cavity of the patient and observing an inside of the second body cavity, the observation device having a manipulator operable by the operator, the manipulator serving as part of the gas delivery channel and being formed with a through hole communicated with the part of the gas delivery channel, and
  wherein the portion of the guide member to which the gas delivery channel is coupled is located closer to the insert portion of the observation device than a portion of the through hole formed in the manipulator.

11. A gas supply apparatus according to claim 10, wherein the manipulator has an insertion opening communicated with the gas delivery channel, the insertion opening allowing a treatment tool to be inserted therethrough, further comprising an adapter including:
  - a coupler to which the guide member is coupled so that the guide member is communicated through the insertion opening with the gas delivery channel; and
  - a slit member defining a slit, the slit being communicated with the insertion opening and allowing a treatment tool being inserted therethrough.

12. A gas supply system for supplying predetermined gas to a first body cavity of a patient through a first delivery member and to a second body cavity of the patient through a second delivery member, the gas supply system comprising:
  - means for switching, according to an operation of a first operation switch by an operator, a first mode for supplying the predetermined gas to the first body cavity and a second mode for supplying the predetermined gas to the second body cavity; and
  - means for:
    - regulating a pressure of the predetermined gas to a first pressure suitable for the first body cavity to only supply to the first body cavity the predetermined gas with its pressure regulated to the first pressure when the means for switching switches to the first mode; and
    - regulating the pressure of the predetermined gas to a second pressure suitable for the second body cavity to only supply to the second body cavity the predetermined gas with its pressure regulated to the second pressure when the means for switching switches to the second mode.

13. A gas supply system according to claim 12, further comprising means for sending an instruction according to an operation of a second operation switch by the operator, wherein the means for regulating is configured to regulate the pressure of the predetermined gas to the second pressure suitable for the second body cavity to supply to the second body cavity the predetermined gas with its pressure regulated to the second pressure only when the means for switching switches to the second mode and the instruction is sent from the means for sending.

14. A gas supply system according to claim 13, wherein, when the instruction is sent from the second operation switch while regulating the pressure of the predetermined gas to the first pressure and supplying the predetermined gas to the first body cavity, the means for regulating is configured to ignore the instruction and continuously executes the regulation of the pressure of the predetermined gas and the supply of the predetermined gas to the first body cavity.

15. An observation system comprising:
  - a gas supply system for supplying predetermined gas to a first body cavity of a patient through a first delivery member and to a second body cavity of the patient through a second delivery member, the gas supply system including:
    - a pressure regulator coupled to the first and second delivery members and configured to regulate a pressure of the predetermined gas to a first pressure and a second pressure, the first pressure being suitable for the first body cavity, the second pressure being suitable for the second body cavity, the pressure regulator allowing the predetermined gas with its pressure regulated to be supplied to both the first and second delivery members;

a first operation switch that switches, when operated by an operator, a first mode and a second mode, in the first mode, the gas supply system being configured such that the predetermined gas with its pressure regulated is only supplied to the first delivery member, in the second mode, the gas supply system being configured such that the predetermined gas with its pressure regulated is only supplied to the second delivery member; and a controller electrically connected to the pressure regulator and the first operation switch and operative to control the pressure regulator according to one of the first and second modes switched by the first operation switch; and an observation device integrated with a gas delivery channel and configured to be inserted into the second body cavity of the patient to observe an inside of the second body cavity, the gas delivery channel serving as part of the second delivery member.

16. An observation system according to claim 15, wherein the gas supply system further comprises a second operation switch operable by the operator, and the controller is operative to:

execute a first control to control the pressure regulator in the first mode so that the predetermined gas is only supplied to the first delivery member and the pressure thereof is regulated to the first pressure to raise a pressure inside the first body cavity up to a predetermined pressure setting or thereabout; and execute a second control to control the pressure regulator in the second mode so that the predetermined gas is switched to the second delivery member and the pressure thereof is switched to the second pressure only when an instruction is sent from the second operation switch operated by the operator.

17. An observation system according to claim 16, wherein, when the instruction is sent from the second operation switch while executing the first control, the controller ignores the instruction and continuously executes the first control.

18. A gas supply system for supplying predetermined gas to an abdominal cavity of a patient through a first delivery member and to a lumen of the patient through a second delivery member, the gas supply system comprising:

a pressure regulator coupled to the first and second delivery members and configured to regulate a pressure of the predetermined gas to a first pressure and a second pressure, the first pressure being suitable for the abdominal cavity, the second pressure being suitable for the lumen, the pressure regulator allowing the predetermined gas with its pressure regulated to be supplied to both the first and second delivery members;

a first operation switch that sets, when operated by an operator, a first mode for the gas supply system, in the first mode, the gas supply system being configured such that the predetermined gas with its pressure regulated is only supplied to the first delivery member;

a second operation switch that sets, when operated by an operator, a second mode for the gas supply system, in the second mode, the gas supply system being configured such that the predetermined gas with its pressure regulated is only supplied to the second delivery member; and a controller electrically connected to the pressure regulator, the first operation switch, and the second operation switch, the controller being configured to, during the gas supply system being in the first mode, control the pressure regulator to regulate the pressure of the predetermined gas to the first pressure until a pressure inside the abdominal cavity rises up to a preset pressure setting independently of an operating state of the second operation switch.

19. A gas supply system for supplying predetermined gas to an abdominal cavity inside a patient through a first delivery member and to a lumen of the patient through a second delivery member, the gas supply system comprising:

means for setting, according to an operation of a first operation switch by an operator, a first mode for supplying the predetermined gas to the first body cavity;

means for setting, according to an operation of a second operation switch by an operator, a second mode for supplying the predetermined gas to the second body cavity;

means for carrying out a first control, during the first mode being set, to regulate a pressure of the predetermined gas to a first pressure suitable for the abdominal cavity to supply only to the abdominal cavity the predetermined gas with its pressure regulated to the first pressure; and means for carrying out a second control, during the second mode being set, regulate the pressure of the predetermined gas to a second pressure suitable for the lumen to supply only to the lumen the predetermined gas with its pressure regulated to the second pressure when the second mode is set, the means for carrying out a first control being configured to continue the first control during the first mode being set until a pressure inside the abdominal cavity rises up to a preset pressure setting independently of an operating state of the second operation switch.

20. An observation system comprising:

a gas supply system for supplying predetermined gas to an abdominal cavity of a patient through a first delivery member and to a lumen of the patient through a second delivery member, the gas supply system including:

a pressure regulator coupled to the first and second delivery members and configured to regulate a pressure of the predetermined gas to a first pressure and a second pressure, the first pressure being suitable for the abdominal cavity, the second pressure being suitable for the lumen, the pressure regulator allowing the predetermined gas with its pressure regulated to be supplied to both the first and second delivery members;

a first operation switch that sets, when operated by an operator, a first mode for the gas supply system, in the first mode, the gas supply system being configured such that the predetermined gas with its pressure regulated is only supplied to the first delivery member;

a second operation switch that sets, when operated by an operator, a second mode for the gas supply system, in the second mode, the gas supply system being configured such that the predetermined gas with its pressure regulated is only supplied to the second delivery member; and a controller electrically connected to the pressure regulator, the first operation switch, and the second operation switch, the controller being configured to, during the gas supply system being in the first mode, control the pressure regulator to regulate the pressure of the predetermined gas to the first pressure until a pressure inside the abdominal cavity rises up to a preset pressure setting independently of an operating state of the second operation switch; and an observation device integrated with a gas delivery channel and configured to be inserted into the lumen of the patient to observe an inside of the lumen, the gas delivery channel serving as part of the second delivery member.

* * * * *